US012703699B2

(12) United States Patent
Gillis et al.

(10) Patent No.: US 12,703,699 B2
(45) Date of Patent: Aug. 11, 2026

(54) INHIBITORS OF HUMAN IMMUNODEFICIENCY VIRUS REPLICATION

(71) Applicant: VIIV HEALTHCARE UK (NO.5) LIMITED, Middlesex (GB)

(72) Inventors: Eric P. Gillis, Branford, CT (US); Christiana Iwuagwu, Wallingford, CT (US)

(73) Assignee: VIIV HEALTHCARE UK (NO. 5) LIMITED, Middlesex (GB)

( * ) Notice: Subject to any disclaimer, the term of this patent is extended or adjusted under 35 U.S.C. 154(b) by 786 days.

(21) Appl. No.: 17/801,410

(22) PCT Filed: Mar. 3, 2021

(86) PCT No.: PCT/IB2021/051765
§ 371 (c)(1),
(2) Date: Aug. 22, 2022

(87) PCT Pub. No.: WO2021/176367
PCT Pub. Date: Sep. 10, 2021

(65) Prior Publication Data

US 2023/0106880 A1 Apr. 6, 2023

Related U.S. Application Data

(60) Provisional application No. 62/985,946, filed on Mar. 6, 2020.

(51) Int. Cl.
*C07D 471/04* (2006.01)
*A61K 9/00* (2006.01)

(52) U.S. Cl.
CPC .......... *C07D 471/04* (2013.01); *A61K 9/0053* (2013.01); *A61K 9/0019* (2013.01)

(58) Field of Classification Search
CPC .................................................... C07D 471/04
See application file for complete search history.

(56) References Cited

U.S. PATENT DOCUMENTS 10,954,252 B1 3/2021 Babu et al.
11,919,897 B2 3/2024 Iwuagwu et al.
(Continued)

FOREIGN PATENT DOCUMENTS

WO WO-2014134566 A2 9/2014
WO WO 2018/203235 A1 11/2018
(Continued)

OTHER PUBLICATIONS

Third Party Observations from Corresponding EP Application No. 21711369.5-1110, dated Jul. 6, 2022.
(Continued)

*Primary Examiner* — Rei Tsang Shiao
(74) *Attorney, Agent, or Firm* — Eric Myers; Nicole Ginanni

(57) ABSTRACT

A compound of Formula I, including pharmaceutically acceptable salts thereof, and compositions and methods for treating human immunodeficiency virus (HIV) infection are set forth:

Formula I (Continued)

-continued

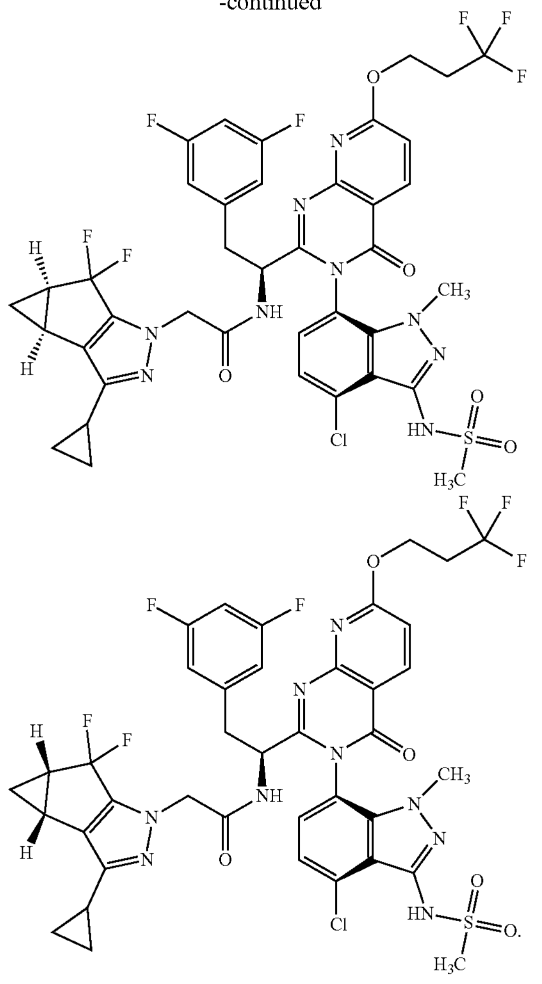

9 Claims, No Drawings

(56) References Cited

U.S. PATENT DOCUMENTS

| | | | |
|---|---|---|---|
| 12,129,255 | B2 | 10/2024 | Gillis et al. |
| 2023/0149408 | A1 | 5/2023 | Parcella et al. |
| 2023/0355626 | A1 | 11/2023 | Gillis et al. |
| 2024/0374598 | A1 | 11/2024 | Bowsher et al. |
| 2025/0019383 | A1 | 1/2025 | Gillis et al. |

FOREIGN PATENT DOCUMENTS

| | | | |
|---|---|---|---|
| WO | WO-2019198024 | A1 | 10/2019 |
| WO | WO-2020031112 | A1 | 2/2020 |
| WO | WO-2020058844 | A1 | 3/2020 |
| WO | WO-2020089778 | A1 | 5/2020 |
| WO | WO-2020095176 | A1 | 5/2020 |
| WO | WO-2020095177 | A1 | 5/2020 |
| WO | WO-2020157692 | A1 | 8/2020 |
| WO | WO-2020254985 | A1 | 12/2020 |
| WO | WO-2021116872 | A1 | 6/2021 |

OTHER PUBLICATIONS

Annex to Third Party Observations from Corresponding EP Application No. 21711369.5-1110, Sep. 6, 2022, XP093105865.

Swallow Steve, Progress in Medicinal Chemistry, 2015 , 54, pp. 97-165, XP093052381.

Eric P. Gillis et al., Journal of Medicinal Chemistry, 58 (21 ), 2015, pp. 8315-8359, XP093035727.

Peter W. Glunz, Bioorg. Med. Chem. Lett. 28 (2), 2017, pp. 53-60, XP085314564.

Steven R LaPlante et al., ChemMedChem, 6 (3), 2011, pp. 505-513, XP072417599.

International Preliminary Report on Patentability for International Application No. PCT/IB2021/051764, mailed Sep. 15, 2022, 11 Pages.

International Preliminary Report on Patentability for International Application No. PCT/IB2021/051765, mailed Sep. 15, 2022, 7 Pages.

International Search Report and Written Opinion for International Application No. PCT/IB2021/051764, mailed May 12, 2021, 13 Pages.

International Search Report and Written Opinion for International Application No. PCT/IB2021/051765 mailed Apr. 15, 2021, 8 Pages.

Mcarthur C., et al., "HIV Capsid Inhibitors Beyond PF74," Diseases, 2019, vol. 7, No. 4, 56, 10 Pages, DOI:10.3390/diseases7040056, XP055800186.

Patani G.A., et al., "Bioisosterism: A Rational Approach in Drug Design," Chemical Reviews, 1996, vol. 96, No. 8, pp. 3147-3176.

Swallow S., "Fluorine in Medicinal Chemistry," Progress in Medicinal Chemistry, 2015, vol. 54, pp. 65-133.

INHIBITORS OF HUMAN IMMUNODEFICIENCY VIRUS REPLICATION

CROSS REFERENCE TO RELATED APPLICATIONS

This application is a § 371 national phase entry of International Application No. PCT/IB2021/051765, filed 3 Mar. 2021, which claims the benefit of U.S. Provisional Application No. 62/985,946, filed 6 Mar. 2020.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. In 2015, an estimated 36.7 million people were living with HIV (including 1.8 million children)—a global HIV prevalence of 0.8%. The vast majority of this number live in low- and middle-income countries. In the same year, 1.1 million people died of AIDS-related illnesses.

Current therapy for HIV-infected individuals consists of a combination of approved anti-retroviral agents. Close to four dozen drugs are currently approved for HIV infection, either as single agents, fixed dose combinations or single tablet regimens; the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INSTIs), or entry inhibitors (one, maraviroc, targets the host CCR5 protein, while the other, enfuvirtide, is a peptide that targets the gp41 region of the viral gp160 protein). In addition, a pharmacokinetic enhancer (cobicistat or ritonavir) can be used in combinations with antiretroviral agents (ARVs) that require boosting.

Despite the armamentarium of agents and drug combinations, there remains a medical need for new anti-retroviral agents. High viral heterogeneity, drug-associated toxicity, tolerability problems, and poor adherence can all lead to treatment failure and may result in the selection of viruses with mutations that confer resistance to one or more antiretroviral agents or even multiple drugs from an entire class (Beyrer, C., Pozniak A. HIV drug resistance—an emerging threat to epidemic control. N. Engl. J. Med. 2017, 377, 1605-1607; Gupta, R. K., Gregson J., et al. HIV-1 drug resistance before initiation or re-initiation of first-line antiretroviral therapy in low-income and middle-income countries: a systematic review and meta-regression analysis. Lancet Infect. Dis. 2017, 18, 346-355; Zazzi, M., Hu, H., Prosperi, M. The global burden of HIV-1 drug resistance in the past 20 years. PeerJ. 2018, DOI 10.7717/peerj.4848). As a result, new drugs are needed that are easier to take, have high genetic barriers to the development of resistance, and have improved safety over current agents. In this panoply of choices, novel mechanisms of action (MOAs) that can be used as part of the preferred antiretroviral therapy (ART) can still have a major role to play since they should be effective against viruses resistant to current agents. The improvements that would make drugs easier to take for long periods of time or even for a lifetime could include all or some of the following: reduced side effects, reduced drug-drug interactions, increased duration between dosing, or alternate routes of administration which match to individual patient preferences. The goals of improved safety would definitely include high therapeutic indices towards any toxicities that would cause discontinuation of dosing, and could also include reduced side-effects or reduced drug-drug interactions. The potential to use fewer overall drugs in a combination regimen would also likely lead to improved compliance and safety. Increased potency against the antiviral target, especially if maintained in the presence of human plasma and serum albumin, would also lead to a reduced dose and could directly and positively affect the duration of dosing and the therapeutic index over side effects and toxicities. To summarize, maximum benefits to HIV infected patients would be achieved if anti-HIV drugs with new mechanisms of action were discovered which also have the other benefits described above which facilitate long term compliance and safety.

Certain potentially therapeutic compounds which appear to act by disrupting the normal functions of the HIV virus capsid have been described in the art. No currently approved drugs act by this mechanism and thus a compound acting through this mechanism would be a useful addition to the options available for the treatment of HIV infection. Compounds which appear to target the HIV capsid have been the subject of recent reviews which describe much of the most important work to date. These reviews include the following: "HIV-1 Capsid Inhibitors as Antiretroviral Agents" Thenin-Houssier, Suzie; Valente, Susana T. Current HIV Research, 2016, 14, 270; "Inhibitors of the HIV-1 capsid, a target of opportunity" Carnes, Stephanie K.; Sheehan, Jonathan H.; Aiken, Christopher, *Current Opinion in HIV & AIDS* 2018, 13, 359-365; "HIV Capsid Inhibitors Beyond PF74" McArthur, Carole, Diseases, 2019, 7, 22; and "Insights into HIV-1 capsid inhibitors in preclinical and early clinical development as antiretroviral agents" Cevik, Muge; Orkin, Chloe *Expert Opin Inv. Drugs,* 2019, 28, 1021; Relevant patent applications are: WO2012065062, WO2013006738, WO 2013006792, WO2014110296, WO2014110297, WO2014110298, WO2014134566, WO2015061518, WO2015130964, WO2015130966, WO2016040084, WO2016033243, WO2016172424, WO2016172425, WO2018035359, WO2018203235, WO2019035904, WO2019035973, WO2019161017, WO2019161280 and WO2019198024.

What is now needed in the art are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, bioavailability and/or reduced frequency of dosing. Also needed are new formulations and methods of treatment which utilize these compounds.

SUMMARY OF THE INVENTION

Briefly, in one aspect, the present invention discloses A compound or salt selected from the group consisting of:

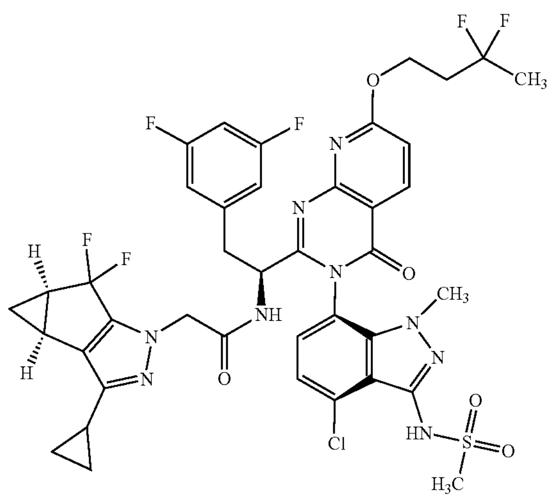

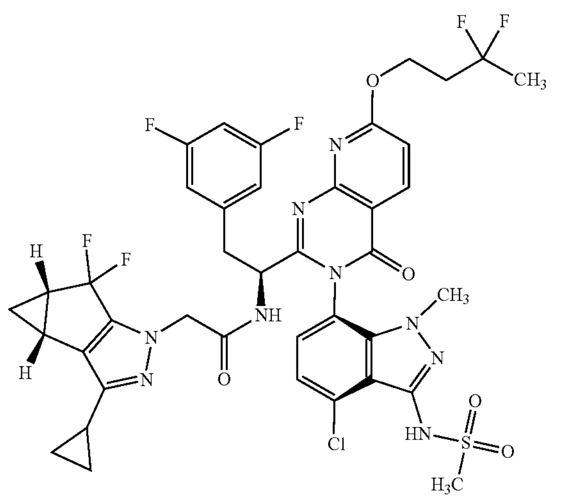

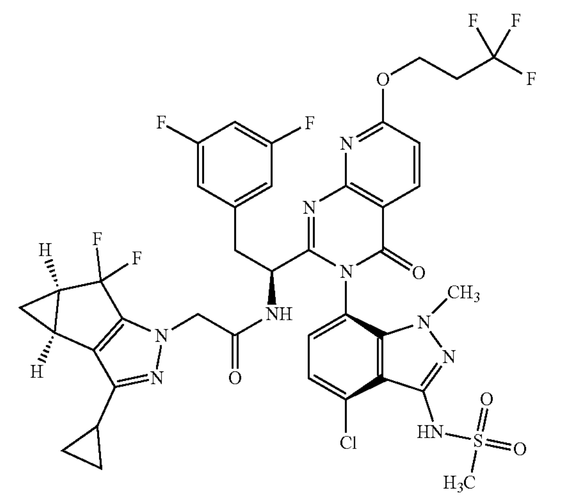

-continued

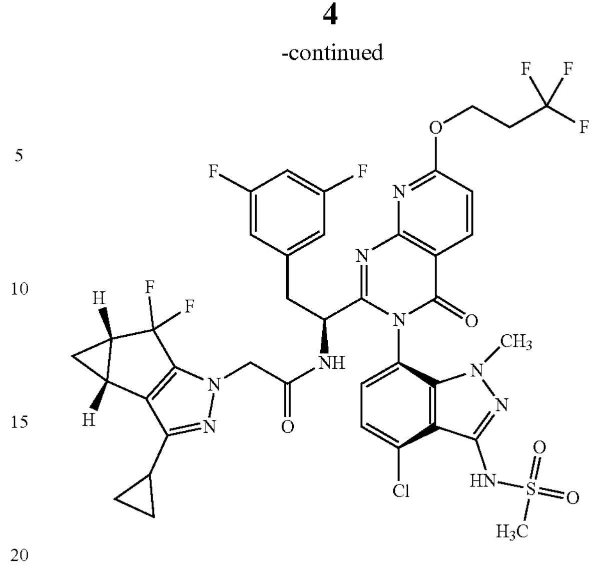

and pharmaceutically acceptable salts thereof.

In another aspect, the present invention discloses a pharmaceutical composition comprising a compound or salt of the invention.

In another aspect, the present invention discloses a method of treating HIV infection in a human comprising administering a compound or salt of the invention.

In another aspect, the present invention discloses a compound or salt of the invention for use in therapy.

In another aspect, the present invention discloses a compound or salt of the invention for use in treating HIV infection in a human.

In another aspect, the present invention discloses the use of a compound or salt of the invention in the manufacture of a medicament for the treatment of HIV infection in a human.

DETAILED DESCRIPTION OF THE INVENTION

The salts of the invention are pharmaceutically acceptable. Such salts may be acid addition salts or base addition salts. For a review of suitable pharmaceutically acceptable salts see, for example, Berge et al, J. Pharm, Sci., 66, 1-19, 1977.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

In one embodiment, the compositions of this invention further comprise a pharmaceutically acceptable excipient. In the method of this invention, preferred routes of administration are oral and by injection to deliver subcutaneously or intramuscularly. Therefore, preferred pharmaceutical compositions include compositions suitable for oral administration (for example tablets) and compositions suitable for subcutaneous or intramuscular injection.

In another aspect the present invention discloses methods of preventing HIV infection in a human or reducing the risk of infection, comprising administering a compound or salt of this invention. Pre-exposure prophylaxis (or PrEP) is when people at risk for HIV infection take daily medicine to lower their chances of getting HIV infection. PrEP has been shown to be effective in reducing the risk of infection.

The compounds and salts of this invention are believed to have as their biological target the HIV capsid and thus their mechanism of action is to modify in one or more ways the function of the HIV capsid.

The compounds and salts of the present invention may be employed alone or in combination with other therapeutic agents. Combination therapies according to the present invention thus comprise the administration of at least one compound or salt of the invention, and the administration of at least one other agent which may be useful in the treatment of HIV infection. A compound or salt of the present invention, and the other agent may be formulated and administered together in a single pharmaceutical composition or may be formulated and administered separately. When formulated and administered separately, administration may occur simultaneously or sequentially in any order. Suitable other agents include, for example, abacavir, atazanavir, bictegravir, cabotegravir, darunavir, delavirdine, didanosine, dideoxyinosine, dolutegravir, doravirine, efavirenz, elvitegravir, emtricitabine, etavirine, fosamprenavir, fostemsavir, indinavir, slatravir, lamivudine, lopinavir, maraviroc, nelfinavir, nevirapine, raltegravir, rilpiverine, ritonavir, saquinavir, stavudine, tipranavir, tenofovir, tenofovir alafenamide, tenofovir disoproxil fumarate, zalcitabine, and zidovudine. Preferred agents include, for example, dolutegravir, bictegravir, islatravir, lamivudine, fostemsavir, and cabotegravir. Particularly preferred agents include, for example, dolutegravir, bictegravir, lamivudine, fostemsavir, and cabotegravir.

EXAMPLES

Preparation of bicyclo[3.1.0]hexan-3-ol

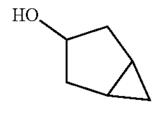

To a stirred solution of cyclopent-3-enol (130 g, 1545 mmol) in DCM (1200 mL) under $N_2$ atmosphere at 0-5° C. was added dropwise a solution of diethyl zinc in hexane (1.0 M, 3091 mL, 3091 mmol) over a period of 3 h. To the solution at 0° C. was added dropwise a solution of diiodomethane (249 mL, 3091 mmol) in DCM (300 mL) over a period of 1 h. The reaction mixture was allowed to warm to 27° C. upon which formation of a white precipitation was observed. The mixture stirred for 16 h. Progress of the reaction was monitored by TLC ($SiO_2$, 20% EtOAc/pet, Rf=0.3, UV-inactive, PMA-active). The reaction mixture was quenched via the careful addition of aq. saturated $NH_4Cl$ solution (1.5 L). The mixture was filtered through pad of Celite. The aqueous layer was extracted with DCM (2×1 L). The combined organic layers were dried over anhydrous $Na_2SO_4$, filtered and then concentrated under reduced pressure to afford crude bicyclo[3.1.0]hexan-3-ol as red liquid, 180 g. $^1$H NMR (400 MHz, $CDCl_3$) δ=4.41-4.35 (m, 1H), 2.18-2.05 (m, 2H), 1.73 (d, J=13.9 Hz, 2H), 1.35-1.25 (m, 2H), 1.21-1.14 (m, 1H), 0.57-0.43 (m, 2H). GCMS: m/z=98.1).

Preparation of bicyclo[3.1.0]hexan-3-one

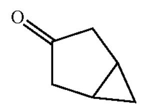

To a stirred solution of bicyclo[3.1.0]hexan-3-ol (210 g, 2054 mmol) in DCM (5000 mL) under $N_2$ atmosphere at 0° C. was added portion-wise Dess-Martin periodinane (954 g, 225 mmol). The mixture was allowed to warm to 27° C. and was then stirred for 16 h. Progress of the reaction was monitored by TLC ($SiO_2$, 20% Acetone/Hex, Rf=0.3, UV in-active, PMA-active). The reaction mixture was filtered through pad of Celite and the filtrate was washed with aq. NaOH (1N, 8×1 L). The combined aqueous phases were extracted with DCM (5×1 L). The combined organic layers were dried over anhydrous $Na_2SO_4$, filtered, and then concentrated under reduced pressure (bath temperature: 20° C.) to afford crude bicyclo[3.1.0]hexan-3-one as brown liquid. The liquid was further purified by downward distillation at 70° C. to afford bicyclo[3.1.0]hexan-3-one as a pale-yellow viscous liquid, 125 g (62%). $^1$H NMR (400 MHz, $CDCl_3$) δ=2.61-2.54 (m, 2H), 2.17-2.12 (m, 2H), 1.54-1.46 (m, 2H), 0.92-0.86 (m, 1H), −0.01-−0.08 (m, 1H); GCMS: M/Z=96.1.

Preparation of 2-(2,2-difluoroacetyl)bicyclo[3.1.0]hexan-3-one

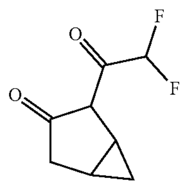 [SMILES: O=C1CC2CC2C1C(=O)C(F)F]

To a stirred solution of bicyclo[3.1.0]hexan-3-one (125 g, 1274 mmol) in THF (1500 mL) under $N_2$ atmosphere at −78° C. was added LDA (2.0 M in THF, 0.701 L, 1402 mmol). The solution was stirred for 1 h at −78° C. To the solution was added slowly over 30 minutes a solution of ethyldifluoroacetate (174 g, 1402 mmol) in THF (300 mL) maintaining a temperature of −78° C. The reaction mixture was allowed to warm to 27° C. and was then stirred for 1 h. Progress of the reaction was monitored by TLC ($SiO_2$, 20% Acetone/Hexane, Rf=0.3, UV-active). The reaction mixture was quenched via the addition of aq. HCl (1N, 2000 mL). The mixture was stirred for 30 min. and then was extracted with EtOAc (3×1000 mL). The combined organic layers were washed with brine (1000 mL), dried over anhydrous $Na_2SO_4$ and filtered. The filtrate was concentrated under reduced pressure to afford 2-(2,2-difluoroacetyl)bicyclo[3.1.0]hexan-3-one as a pale-yellow viscous liquid, 180 g (71%). $^1H$ NMR (400 MHz, $CDCl_3$) δ=6.18 (t, J=54.8 Hz, 1H), 2.70-2.62 (m, 1H), 2.35 (d, J=19.4 Hz, 1H), 2.14 (br s, 1H), 1.26-1.21 (m, 1H), 1.04-1.03 (m, 1H), 0.22-0.21 (m, 1H), LCMS: M/Z=173.17).

Preparation of ethyl 2-(3-(difluoromethyl)-3b,4,4a,5-tetrahydro-1H-cyclopropa[3,4]cyclopenta[1,2-c]pyrazol-1-yl)acetate

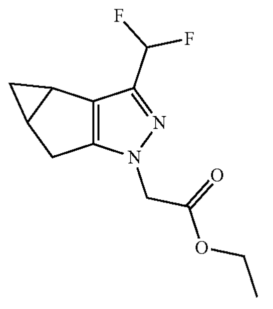 [SMILES: CCOC(=O)Cn1nc(C(F)F)c2c1CC1CC21]

To a stirred solution of 2-(2,2-difluoroacetyl)bicyclo[3.1.0]hexan-3-one (180 g, 910 mmol) in ethanol (2 L) under $N_2$ atmosphere at 27° C. was added ethyl 2-hydrazinylacetate hydrochloride (422 g, 2729 mmol) followed by sulfuric acid (20 mL, 375 mmol). The mixture was stirred for 30 min. and then was heated to 100° C. and stirred for 16 h. Progress of the reaction was monitored by TLC ($SiO_2$, 20% Acetone/Hexane, Rf=0.3, UV-active). The reaction mixture was concentrated under reduced pressure. The residue was dissolved in EtOAc (2000 mL) and was washed with water (2×1 L), brine (1.0 L), dried over anhydrous $Na_2SO_4$, filtered, and then was concentrated under reduced pressure. The resulting residue was subjected to silica gel column chromatography (pet.:acetone 100:0→98:2) to afford ethyl 2-(3-(difluoromethyl)-3b,4,4a,5-tetrahydro-1H-cyclopropa[3,4]cyclopenta[1,2-c]pyrazol-1-yl)acetate as an off-white solid, 110 g (46%). $^1H$ NMR (400 MHz, DMSO-$d_6$) δ=6.86 (t, J=54.8 Hz, 1H), 4.93 (s, 2H), 4.14 (q, J=7.2 Hz, 2H), 2.88-2.79 (m, 1H), 2.76-2.68 (m, 1H), 2.14-2.04 (m, 2H), 1.19 (t, J=7.2 Hz, 3H), 1.10-1.03 (m, 1H), 0.14 (q, J=4.3 Hz, 1H).

Preparation of ethyl 2-(3-(difluoromethyl)-5-oxo-3b,4,4a,5-tetrahydro-1H-cyclopropa[3,4]cyclopenta[1,2-c]pyrazol-1-yl)acetate

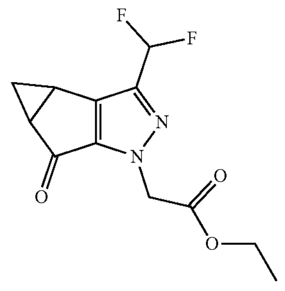 [SMILES: CCOC(=O)Cn1nc(C(F)F)c2c1C(=O)C1CC21]

To a stirred solution of ethyl 2-(3-(difluoromethyl)-3b,4,4a,5-tetrahydro-1H-cyclopropa[3,4]cyclopenta[1,2-c]pyrazol-1-yl)acetate (110 g, 422 mmol) and Celite (395 g) in cyclohexane (3.5 L) at 0° C. was added portionwise pyridinium dichromate (794 g, 2110 mmol). To the mixture under nitrogen atmosphere was added dropwise tert-butyl hydroperoxide (355 mL, 2130 mmol) over a period of 10 min. The reaction mixture was warmed to 27° C. and was then stirred at that temperature for 48 h. Progress of the reaction was monitored by TLC ($SiO_2$, 30% Acetone/pet, Rf=0.4, UV-active). The reaction mixture was filtered, and the filter cake was extracted with EtOAc (1000 mL). The filtrate was washed with saturated aq. $Na_2S_2O_3$ (2×500 mL); saturated aq. $FeSO_4$ (300 mL); and then brine (500 mL). The organic layer was dried over anhydrous $Na_2SO_4$; filtered and concentrated under reduced pressure to obtain the crude title compound (150 g).

Preparation of ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate

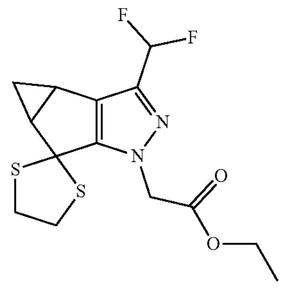 [SMILES: CCOC(=O)Cn1nc(C(F)F)c2c1C1(SCCS1)C1CC21]

To a stirred solution of ethyl 2-(3-(difluoromethyl)-5-oxo-3b,4,4a,5-tetrahydro-1H-cyclopropa[3,4]cyclopenta[1,2-c]pyrazol-1-yl)acetate (75 g, 269 mmol) in DCM (1500 mL) at 27° C. under nitrogen atmosphere was added ethane-1,2- dithiol (43.0 mL, 511 mmol) followed by the addition of boron trifluoride acetic acid (72.6 mL, 511 mmol). The solution was stirred for 16 h. Progress of the reaction was monitored by TLC ($SiO_2$, 20% Acetone/Pet, Rf=0.35, UV-Active). After completion, the reaction mixture was cooled to 0° C. and quenched via the addition of aq. saturated $NaHCO_3$ (500 mL). The mixture was extracted with DCM (2×1000 mL). The combined organics were washed with brine (1000 mL), dried over anhydrous $Na_2SO_4$, filtered and concentrated under reduced pressure to obtain a brown liquid. This material was subjected to silica gel column chromatography (Pet.:EtOAc 95:5→90:10) to afford ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate as an off-white solid, 80 g (74%). $^1$H-NMR (400 MHz, $CDCl_3$) δ=6.61 (t, J=55.2 Hz, 1H), 5.00-4.85 (m, 2H), 4.29-4.19 (m, 2H), 3.55-3.46 (m, 4H), 2.63-2.53 (m, 1H), 2.49-2.38 (m, 1H), 1.30-1.24 (m, 4H), 0.65-0.60 (m, 1H). LCMS M+H=346.9.

Preparation of ethyl 2-(3-(difluoromethyl)-5,5-difluoro-3b,4,4a,5-tetrahydro-11 cyclopropa[3,4]cyclopenta[1,2-c]pyrazol-1-yl)acetate

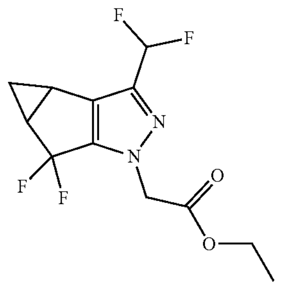 [SMILES: CCOC(=O)Cn1nc(C(F)F)c2c1C(F)(F)C1CC21]

To a stirred solution of 1,3-dibromo-5,5-dimethylimidazolidine-2,4-dione (26.3 g, 92 mmol) in DCM (20 mL) at −70° C. under $N_2$ atmosphere was added HF-pyridine (2.460 g, 24.83 mmol).

The solution was for 30 min. To the solution was added a solution of ethyl 2-(3-(difluoromethyl)-4,4a-dihydrospiro[cyclopropa[3,4]cyclopenta[1,2-c]pyrazole-5,2'-1,3]dithiolane]-1(3bH)-yl)acetate (10 g, 25 mmol) in DCM (20 mL). The reaction mixture was allowed to warm to −40° C. and then was stirred at that temperature for 1 h. Progress of the reaction was monitored by TLC ($SiO_2$, 30% EtOAc/Pet, Rf=0.3, UV in-active). The reaction mixture was quenched via the addition of aq. sat. $NaHCO_3$ (200 mL). The mixture was warmed to room temperature and was then extracted with EtOAc (2×100 mL). The combined organics were washed with brine (50 mL); dried over anhydrous $Na_2SO_4$; filtered; and were concentrated under reduced pressure to afford a brown solid. This material was subjected to silica gel column chromatography (Pet.:EtOAc 100:0→75-25) to afford ethyl 2-(3-(difluoromethyl)-5,5-difluoro-3b,4,4a,5-tetrahydro-1H-cyclopropa[3,4]cyclopenta[1,2-c]pyrazol-1-yl)acetate as a pale yellow solid, 8.5 g (91%). $^1$H NMR (400 MHz, $CDCl_3$) δ=6.62 (t, =55.2 Hz, 1H), 4.82 (s, 2H), 4.30-4.18 (m, 2H), 2.51-2.37 (m, 2H), 1.42-1.35 (m, 1H), 1.31-1.23 (m, 3H), 1.14-1.08 (m, 1H). LCMS M+H=293.07.

Preparation of 2-(3-(difluoromethyl)-5,5-difluoro-3b,4,4a,5-tetrahydro-1H-cyclopropa[3,4]cyclopenta[1,2-c]pyrazol-1-yl)acetic acid

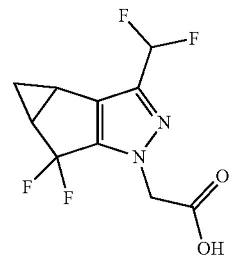 [SMILES: O=C(O)Cn1nc(C(F)F)c2c1C(F)(F)C1CC21]

To a stirred solution of ethyl 2-(3-(difluoromethyl)-5,5-difluoro-3b,4,4a,5-tetrahydro-1H-cyclopropa[3,4]cyclopenta[1,2-c]pyrazol-1-yl)acetate (15 g, 50 mmol) in THF (17 mL) and MeOH (66 mL) at 0° C. under $N_2$ atmosphere was added a solution of LiOH (1.788 g, 74.7 mmol) in water (66 mL). The reaction mixture was allowed to warm to 27° C. and was then stirred for 3 h at that temperature. Progress of the reaction was monitored by TLC ($SiO_2$, 5% MeOH/DCM, Rf=0.2, UV Active). After completion, the reaction mixture was concentrated under reduced pressure; diluted with water (50 mL); and washed with EtOAc (2×250 mL) to remove impurities. The aqueous layer was adjusted to pH 2-3 using aq. HCl (1M), then was extracted with EtOAc (3×1000 mL). The combined organics were dried over anhydrous $Na_2SO_4$; filtered; and concentrated under reduced pressure to afford 2-(3-(difluoromethyl)-5,5-difluoro-3b,4,4a,5-tetrahydro-1H-cyclopropa[3,4]cyclopenta[1,2-c]pyrazol-1-yl)acetic acid as an off white solid, 14 g (98%). LCMS M+H=265.15.

Separation affording 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid

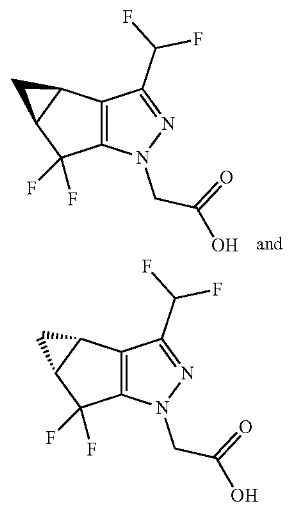
and 2-(3-(difluoromethyl)-5,5-difluoro-3b,4,4a,5-tetrahydro-1H-cyclopropa[3,4]cyclopenta[1,2-c]pyrazol-1-yl)acetic acid (5.5 g) was dissolved in isopropanol (20 mL). The solution was subjected portion-wise to SFC chiral separation as follows: Instrument=Thar 80; column=Chiralpak IC 30×250 mm, 5 micron; solvent A=super critical $CO_2$; solvent B=isopropanol with 0.5% isopropylamine (v/v); eluent composition=70% A:30% B; flow-rate=65 g/min; back-pressure=100 bar; temperature=30° C.; injection volume=2.5 mL; detection=220 nm. 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid was collected as peak eluting from 7.5 min. to 14 min; 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid was collected as a peak eluting from 2.7 min. to 5.8 min. For each enantiomer, the resulting solution was concentrated under reduced pressure and the resulting solids were dissolved in EtOAc, then twice washed with aq. citric acid (1M) followed by water followed by brine. The organic solution was dried over $Na_2SO_4$; filtered; then concentrated in vacuo to afford the separated enantiomer in 80-90% recovery.

Preparation of 2-((3bS,4aR)-3-cyclopropyl-5,5-difluoro-3b,4,4a,5-tetrahydro-1H-cyclopropa[3,4]cyclopenta[1,2-c]pyrazol-1-yl)acetic acid and 2-((3bR,4aS)-3-cyclopropyl-5,5-difluoro-3b,4,4a,5-tetrahydro-1H-cyclopropa[3,4]cyclopenta[1,2-c]pyrazol-1-yl)acetic acid

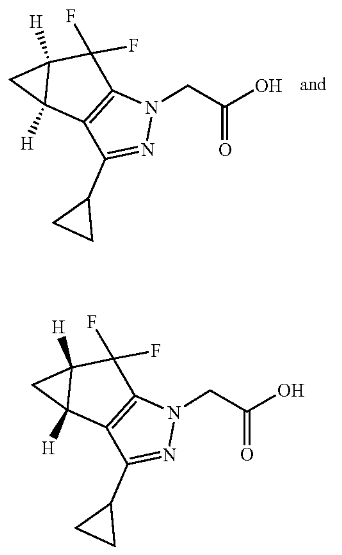

The title compounds were prepared following the route and procedures used to prepare 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid but substituting cyclopropanecarbonyl chloride for ethyldifluoroacetate. The route is depicted in the scheme below.

Synthesis Scheme:

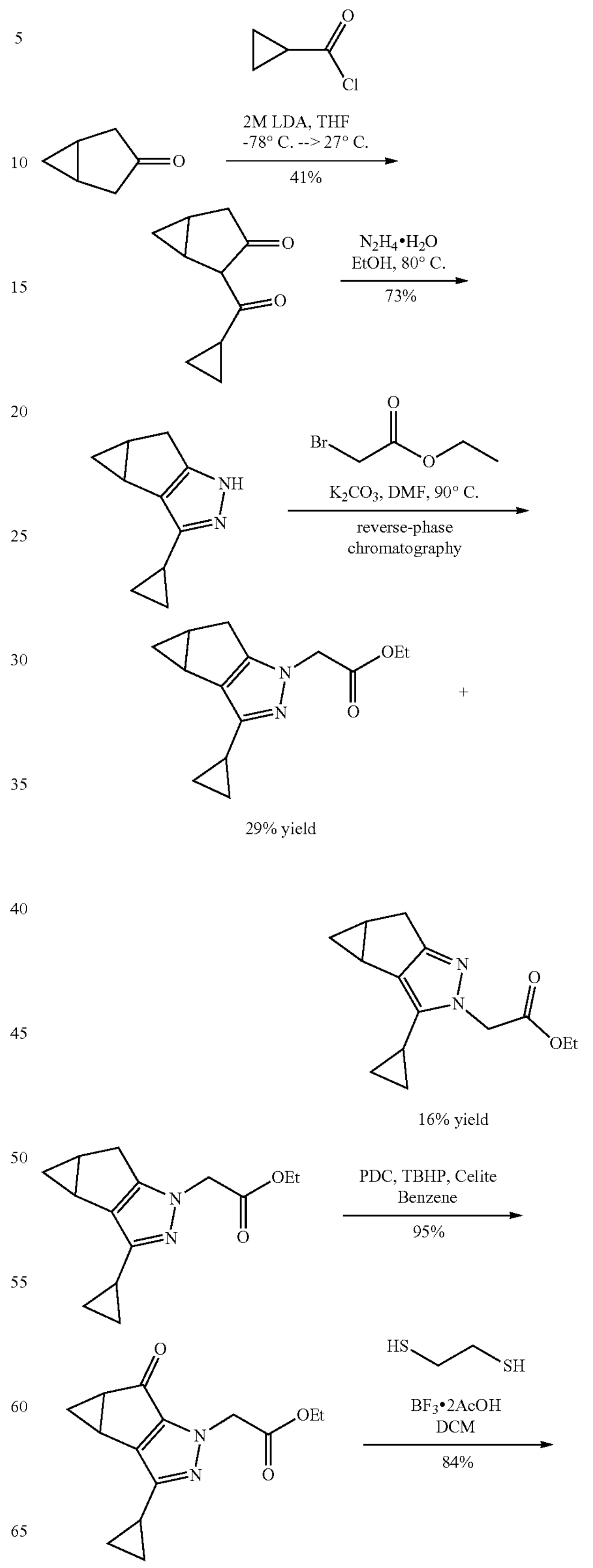

-continued
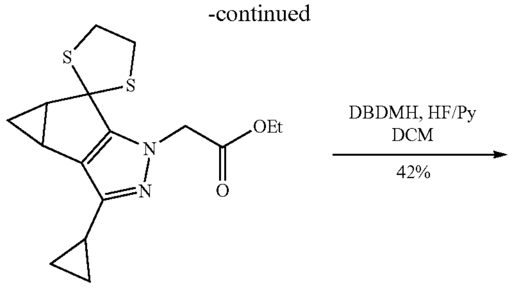
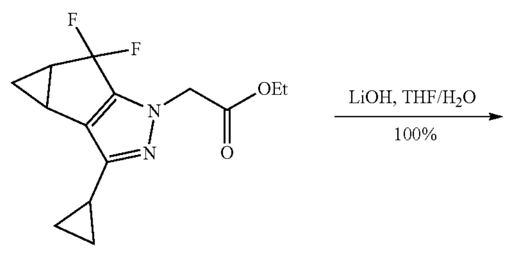
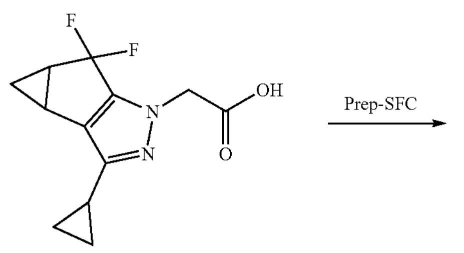
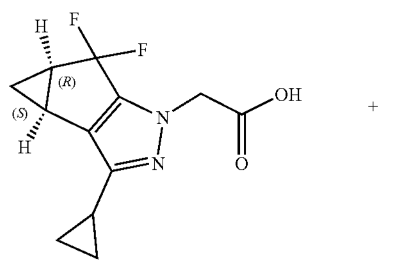
+
33% yield
2-((3bS,4aR)-3-cyclopropyl-5,5-difluoro-3b,4,4a,5-tetrahydro-1H-cyclopropa[3,4]cyclopenta[1,2-c]pyrazol-1-yl)acetic acid
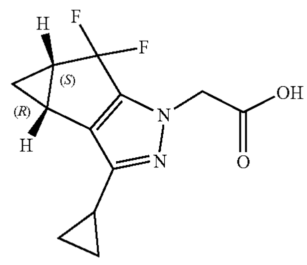
33% yield
2-((3bR,4aS)-3-cyclopropyl-5,5-difluoro-3b,4,4a,5-tetrahydro-1H-cyclopropa[3,4]cyclopenta[1,2-c]pyrazol-1-yl)acetic acid
Preparation of N-(7-amino-4-chloro-1-methyl-1H-indazol-3-yl)-N-(4-methoxybenzyl)methanesulfonamide
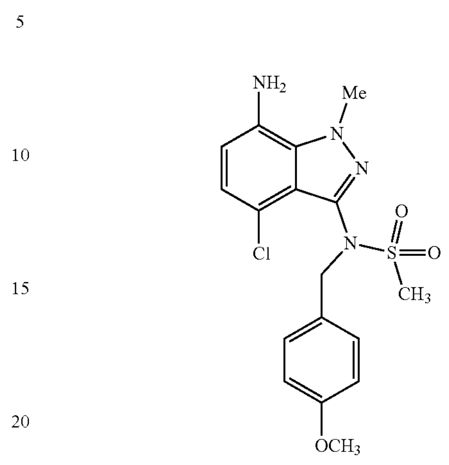
Synthesis Scheme:
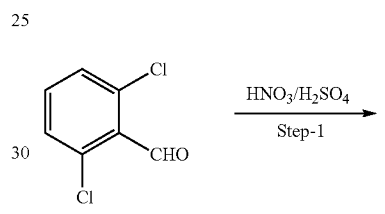
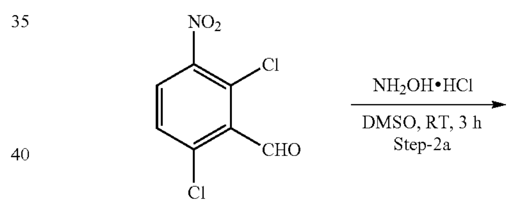
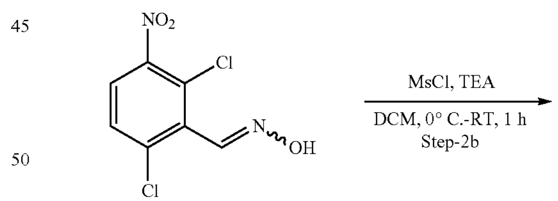
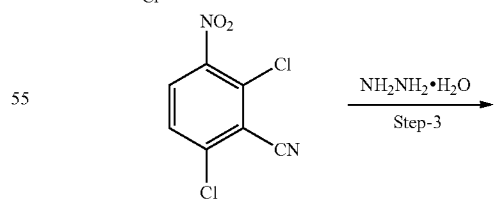
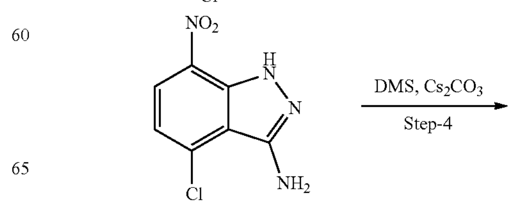

-continued

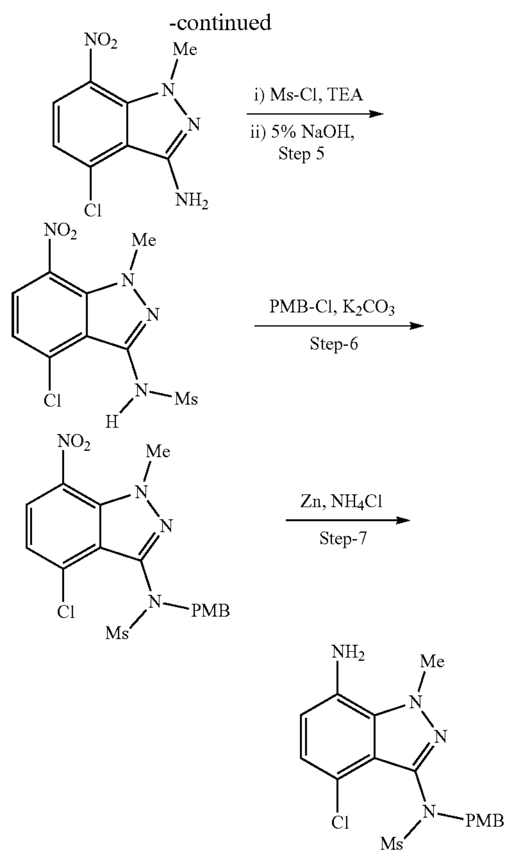

Step 1: Preparation of 2,6-dichloro-3-nitrobenzaldehyde

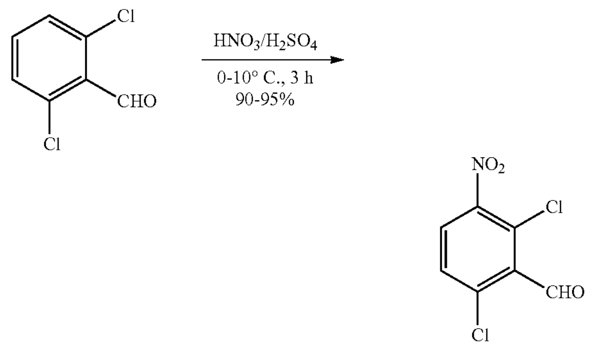

To a solution of sulfuric acid ($H_2SO_4$) (5.63 L, 4.5 V) in a round-bottom flask at 0-5° C. was added 2,6-dichlorobenzaldehyde (1.25 kg, 7.10 mol, 1.0 equiv.) in portions at below 15° C. The reaction mass was stirred at 0-5° C. for 30 min. A solution of freshly prepared nitration mixture [Prepared from Conc. $H_2SO_4$ (0.425 L, 0.34 V) and 70% $HNO_3$ (0.85 kg, 13.49 mol, 1.30 equiv.) at 0° C.] was added to the above reaction mixture at below 10° C. [Note: Reaction is slightly exothermic (3-6° C.); so that addition is preferred at lower temperature]. The reaction mixture was stirred at 5-10° C. for 2-3 h. After completion of the reaction (monitored by TLC), it was quenched with ice cold water (18.75 L, 15 V) at below 25° C. Then the reaction mass was allowed warm to room temperature and stirred for 2 h. The solids were isolated by filtration and then were washed with water (2.5 L, 2.0 V). Bulk residual water was removed from the solids by maintaining vacuum filtration for 60-90 min. The crude wet solid was initially dried under air atmosphere; then in a hot air oven at 50-55° C. for 10-12 h (until moisture content is not more than 5.0%) to get the dried title product, 2,6-dichloro-3-nitrobenzaldehyde (1.44 kg, 92% yield) as a yellow solid. $^1H$ NMR (400 MHz, $CDCl_3$): δ 10. 44 (s, 1H), 7.88 (d, J=8.4 Hz, 1H), 7.56 (d, J=8.8 Hz, 1H).

Step 2: Preparation of 2,6-dichloro-3-nitrobenzonitrile

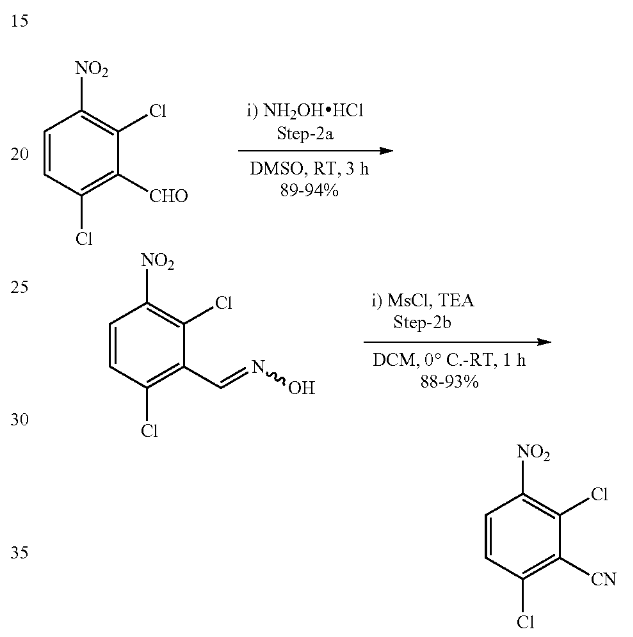

(Step-2a) To a solution of DMSO (5.9 L, 5.0 V)) in a round-bottom flask was added 2,6-dichloro-3-nitrobenzaldehyde (1.17 kg, 5.31 mol, 1.0 equiv.) at room temperature. After being stirred for 30 min at room temperature, hydroxylamine hydrochloride (0.63 kg, 9.04 mol, 1.70 equiv.) was added and the reaction mass was stirred at room temperature for 3 h. After completion of the reaction (monitored by TLC), the reaction mass was quenched by the addition of ice-cold water (18.0 L, 15.0 V) added at a rate sufficient to maintain the temperature below 30° C. (Observation: Solids formed upon water addition). The reaction mass was stirred at room temperature for 60-90 min. The solids were isolated by filtration; washed with water (2.5 L, 2.0 V); followed by washing with a mixture of acetone and hexanes (6.0 L, 1:1 ratio). Bulk residual water was removed from the solids by maintaining vacuum filtration for 60-90 min. The wet solid was initially air dried and then finally dried in a hot air oven at 50-55° C. for 10-12 h (until moisture content was not more than 1.0%) to get the dried target product, 2,6-dichloro-3-nitrobenzaldehyde oxime (1.22 kg, 92% yield) as an off-white solid. The crude product (which contains 10-20% of 2,6-dichloro-3-nitrobenzonitrile) was used directly in the next step without further purification.

(Step-2b) To a stirred solution of the crude oxime (preparation described above, 1.13 kg, 4.80 mol, 1.0 equiv.) in DCM (9.04 L, 8.0 V) at 0-5° C. was added triethylamine ("TEA", 1.02 kg, 10.09 mol, 2.1 equiv.). After being stirred for 5 min, methanesulfonyl chloride (0.60 kg, 5.29 mol, 1.1 equiv.) was added (Observation: An exotherm is noted during the addition) slowly at 15° C. Then the reaction mass was stirred at room temperature for 30-45 min. After completion of the reaction (progress of reaction was monitored by TLC; mobile phase: 20% ethyl acetate in hexanes), the reaction mass was diluted with water (6.78 L, 6.0 V); the organic layer was separated; and the aqueous layer was extracted with DCM (3.4 L, 3.0 V). The combined organic layers were washed with brine (5.65 L, 5.0 V); dried over $Na_2SO_4$; and concentrated under vacuum. The resulting crude solids were triturated with hexanes (4.50 L, 4.0 V) at room temperature. The wet material was dried in a hot air oven at 50-55° C. for 5-6 h to get the dried product, 2,6-dichloro-3-nitrobenzonitrile (0.95 kg, 91% yield) as a yellow solid. $^1$H NMR (400 MHz, $CDCl_3$): δ 8.07 (d, J=8.8 Hz, 1H), 7.63 (d, J=8.8 Hz, 1H).

Step 3: Preparation of 4-chloro-7-nitro-1H-indazol-3-amine

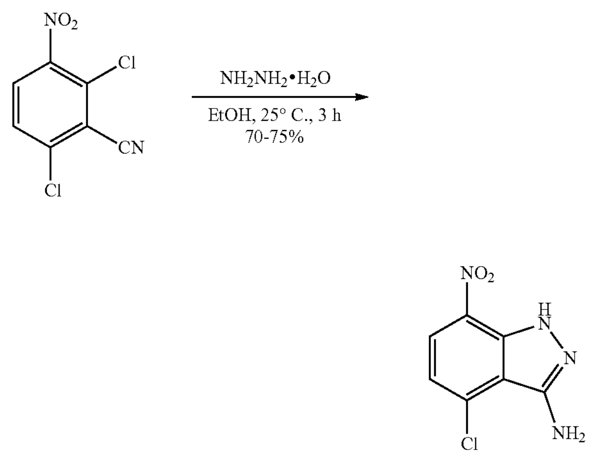

To a stirred solution of 2,6-dichloro-3-nitrobenzonitrile (750.0 g, 3.45 mol, 1.0 equiv.) in ethanol (7.5 L, 10.0 V) at 15-20° C. was slowly added hydrazine hydrate (519.0 g, 10.36 mol, 3.0 equiv.) while maintaining the reaction mass below 25° C. (Observation: Addition is slightly exothermic and solid formation will begin upon addition). The reaction mixture temperature was slowly raised to room temperature and then the mixture was stirred for 3 h (Observation: the quantity of solids will increase during this time). After completion of the reaction (monitored by TLC), the mixture was diluted with water (7.5 L, 10.0 V) and further stirred for 1 h at room temperature. The solids were isolated via filtration and then were washed with water (2.25 L, 3.0 V). The wet solid was washed with a 1:1 ratio mixture of acetone (1.875 L, 2.5 V) and hexanes (1.875 L, 2.5 V). Bulk residual water was removed from the solids by maintaining vacuum filtration for 60-90 min. The wet solid was finally dried in a hot air oven for 7-8 h at 50° C. (until moisture content reaches below 1.5%) to get the dried product, 4-chloro-7-nitro-1H-indazol-3-amine (549.0 g, 75% yield) as a brick red-colored solid. $^1$H NMR (400 MHz, $CDCl_3$): δ 10.36 (bs, 1H), 8.20 (d, J=8.4 Hz, 1H), 7.07 (d, J=8.40 Hz, 1H), 4.73 (bs, 2H).

Step 4: Preparation of 4-chloro-1-methyl-7-nitro-1H-indazol-3-amine

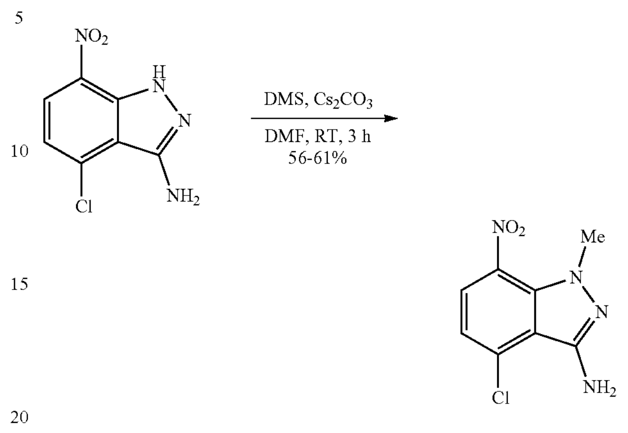

To a stirred solution of 4-chloro-7-nitro-1H-indazol-3-amine (500 g, 0.42 mol, 1.0 equiv.) in DMF (5.0 L, 10.0 V) at 5-10° C. was slowly added cesium carbonate ($Cs_2CO_3$) (1.91 kg, 5.88 mol, 2.5 equiv.) while maintaining the reaction mass below 10° C. After being stirred for 5-10 min, dimethyl sulphate (326.3 g, 2.59 mol, 1.1 equiv.) was added while maintaining the reaction mass below 10° C. (Note: Slow addition is preferred for obtaining more favorable regio-selectivity). Then, the reaction temperature was slowly raised to room temperature and stirring was continued an additional 2 h at the same temperature. After completion of the reaction (monitored by TLC), the reaction mass was quenched by the addition of ice-cold water (15.0 L, 30.0 V) and the resulting mixture was then stirred for 6-8 h at room temperature. The solids were isolated via filtration and were then washed with water (1.5 L, 3.0 V). The wet solid was washed with IPA (1.5 L, 3.0 V) followed by hexanes (1.0 L, 2.0 V). Bulk residual water was removed from the solids by maintaining vacuum filtration for 60-90 min. The wet solid was dried in a hot air oven for 7-8 h at 50° C. (until moisture content is below 1.0%). The isolated material, 4-chloro-1-methyl-7-nitro-1H-indazol-3-amine (319.0 g, 60% yield), was used in the next step without further purification. $^1$H NMR (400 MHz, $CDCl_3$): δ 7.97 (d, J=8.32 Hz, 1H), 6.97 (d, J=8.24 Hz, 1H), 4.63 (bs, 2H), 3.96 (s, 3H).

Step 5: Preparation of N-(4-chloro-1-methyl-7-nitro-1H-indazol-3-yl)methanesulfonamide

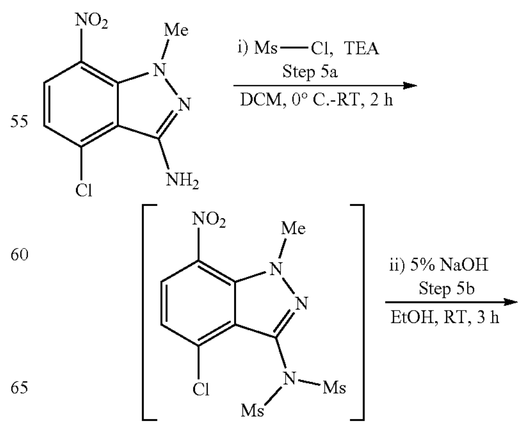

-continued

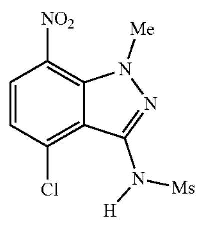

(Step 5a) To a solution of 4-chloro-1-methyl-7-nitro-1H-indazol-3-amine (625.0 g, 2.76 mol, 1.0 equiv.) in DCM (6.25 L, 10.0 V) at 0-5° C. was added triethylamine (TEA) (837.0 g, 8.27 mol, 3.0 equiv.); followed by the addition of 4-dimethylaminopyridine (DMAP) (20.60 g, 0.165 mol, 0.06 equiv.). The reaction mass was stirred for 5-10 min., then methanesulfonyl chloride (MsCl) (790.0 g, 6.89 mol, 2.5 equiv.) added slowly while maintaining the reaction mass below 10° C. The reaction mixture was allowed to warm to room temperature and was then stirred for 1.5-2.0 h. After completion of the reaction (monitored by TLC), the mixture was diluted with water (6.25 L, 10.0 V) and then stirred at room temperature for 15 min. The organic layer was separated, and the aqueous layer was extracted with DCM (6.25 L, 10.0 V). The combined organic layers were washed with brine (1.25 L, 2.0 V), dried over $Na_2SO_4$ and concentrated to get the crude solids. The solids were triturated with hexanes (1.25 L, 2.0 V) at room temperature to obtain the intermediate, N-(4-chloro-1-methyl-7-nitro-1H-indazol-3-yl)-N-(methylsulfonyl)methanesulfonamide, which was used directly in the next step.

(ii) To a stirred solution of N-(4-chloro-1-methyl-7-nitro-1H-indazol-3-yl)-N-(methylsulfonyl)methanesulfonamide (prepared above) in ethanol (10.5 L, 20.0 V) at room temperature was added slowly an aq. 5% NaOH solution (4.38 L, 7.0 V) [Note: Slow addition is preferred via dropping funnel]. The reaction mass was stirred at the same temperature for 3 h. After completion of the reaction (monitored by TLC) [Sample preparation for TLC analysis: ~1.0 ml of sample acidified with aq. 2.0 N HCl to reach the pH: 2-3, extract it with ethyl acetate and analyze the organic layer by TLC], the reaction mass was cooled to 0-5° C. and the pH was adjusted to 2-3 by the addition of aq. 2.0 N HCl (3.13 L, 5.0 V) while maintain the reaction temperature below 10° C. [Note: Precipitation occurred upon addition of HCl and increased with stirring]. The reaction mixture was warmed to room temperature and then stirred for 1.5-2.0 h. Solids obtained were isolated via filtration and were then washed with water (1.25 L, 2.0 V); followed by washing with hexanes (1.25 L, 2.0 V). Bulk residual water was removed from the solids by maintaining vacuum filtration for 60-90 min. The wet material was dried in a hot air oven at 50° C. for 6-7 h (Until the moisture content is below 1.0%) to get the dried product, N-(4-chloro-1-methyl-7-nitro-1H-indazol-3-yl)methanesulfonamide (640.0 g, 76%) as a yellow solid. $^1$H NMR (400 MHz, $CDCl_3$): δ 8.05 (d, J=8.32 Hz, 1H), 7.32 (bs, 1H), 7.17 (d, J=8.28 Hz, 1H), 4.15 (s, 3H), 3.45 (s, 3H).

Step 6: Preparation of N-(4-chloro-1-methyl-7-nitro-1H-indazol-3-yl)-N-(4-methoxybenzyl)methanesulfonamide

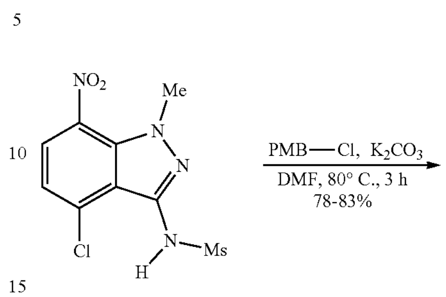

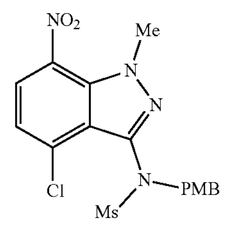

To a mixture of N-(4-chloro-1-methyl-7-nitro-1H-indazol-3-yl)methanesulfonamide (635.0 g, 2.08 mol, 1.0 equiv.) and 1-(chloromethyl)-4-methoxybenzene (359.0 g, 2.30 mol, 1.1 equiv.) in DMF (6.35 L, 10.0 V) at room temperature was added potassium carbonate (374.7 g, 2.70 mol, 1.3 equiv.). The reaction mixture was heated to 80-90° C. and maintained at that temperature for 3 h. After completion of the reaction (monitored by TLC), the mixture was poured into ice cold water (19.05 L, 30.0 V) [Note: Slow quenching with vigorous stirring is preferred to avoid clumping as the product precipitates]. The resulting solids were isolated via filtration and washed with water (1.90 L, 3.0 V); then the solids were washed with hexanes (1.27 L, 2.0 V). Bulk residual water was removed from the solids by maintaining vacuum filtration for 60-90 min. The isolated solid was dissolved in Ethyl acetate (12.7 L, 20.0 V) and charcoal was added (63.5 g). The mixture was heated to 60-70° C. and then stirred for 30-45 min. at that temperature. The mixture was filtered while still hot (40-50° C.) through a pad of Celite and the Celite pad was then extracted with ethyl acetate (3.17 L, 5.0 V). The combined filtrates were concentrated to dryness under reduced pressure at below 50° C. Ethyl acetate (0.635 L, 1.0 V) was added to the solids at room temperature. The resultant solid suspension was stirred for 30 min. The solids were isolated via filtration and then were washed with hexanes (1.27 L, 2.0 V). Residual water was removed from the solids by maintaining vacuum filtration for 45-60 min. to afford the product N-(4-chloro-1-methyl-7-nitro-1H-indazol-3-yl)-N-(4-methoxybenzyl) methane sulfonamide (705.0 g, 80% yield) as a yellow solid. $^1$H NMR (400 MHz, $CDCl_3$): δ 7.99 (d, J=8.24 Hz, 1H), 7.27 (d, J=8.68 Hz, 2H), 7.19 (d, J=8.24 Hz, 1H), 6.80 (d, J=8.44 Hz, 2H), 4.95-4.76 (m, 2H), 4.17 (s, 3H), 3.76 (s, 3H), 3.01 (s, 3H).

Step 7: Preparation of N-(7-Amino-4-chloro-1-methyl-1H-indazol-3-yl)-N-(4-methoxybenzyl)methanesulfonamide

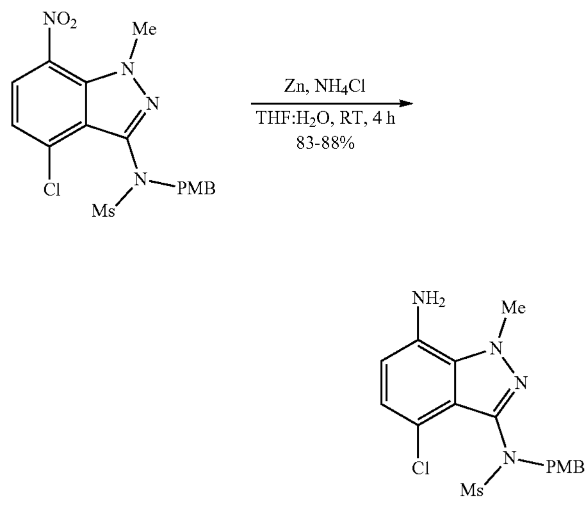

To a stirred suspension of zinc powder (540.0 g, 8.23 mol, 10.0 equiv.) in a mixture of THF (3.50 L, 10.0 V) and water (7.0 L, 20.0 V) at room temperature was added ammonium chloride ($NH_4Cl$) (449.0 g, 8.23 mol, 10.0 equiv.). To the mixture was added N-(4-chloro-1-methyl-7-nitro-1H-indazol-3-yl)-N-(4-methoxybenzyl)methanesulfonamide (350 g, 0.823 mol, 1.0 equiv.) in THF (7.0 L, 20.0 V). The reaction mixture was stirred at room temperature for 3-4 h. After completion of the reaction (monitored by in-process TLC/HPLC), the mixture was diluted with ethyl acetate (3.5 L, 10.0 V) and water (1.12 L, 2.5 V). The mixture was stirred for 15 min. The reaction mass was filtered through a pad of Celite bed washing with ethyl acetate (1.75 L, 5.0 V). The bi-phasic filtrate was collected, and the phases were separated. The aqueous layer was extracted with ethyl acetate (3.50 L, 10.0 V). The combined organic layers were washed with brine (3.50 L, 10 V), dried over $Na_2SO_4$, and then concentrated in vacuo to afford a crude solid. To the crude product was added MTBE (3.25 L, 10 V) and the suspension was stirred for 30 min at room temperature. The solids were isolated by filtration. Bulk residual water was removed from the solids by maintaining vacuum filtration for 30-45 min. The wet product was dried in a hot air oven (50° C.) for 2 h to afford the title product, N-(7-amino-4-chloro-1-methyl-1H-indazol-3-yl)-N-(4-methoxybenzyl)methanesulfonamide (276.0 g, 85% yield) as off-white solid. $^1H$ NMR (400 MHz, $CDCl_3$): δ 7.29-7.26 (m, 2H), 6.86-6.79 (m, 2H), 6.42 (d, J=7.80 Hz, 1H), 4.99-4.70 (m, 2H), 4.25 (s, 3H), 3.77 (s, 5H), 2.98 (s, 3H).

Preparation of 3,3-difluorobutan-1-ol

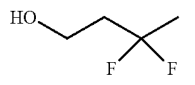

Synthesis Scheme:

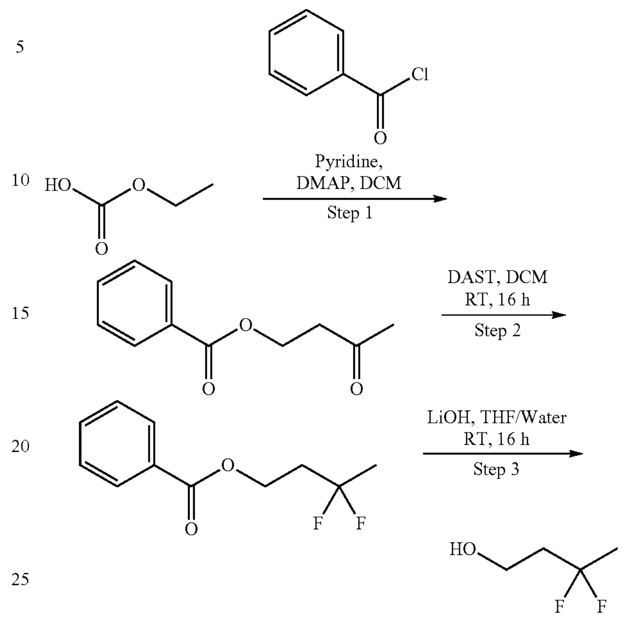

Step 1: Preparation of 3-oxobutyl benzoate

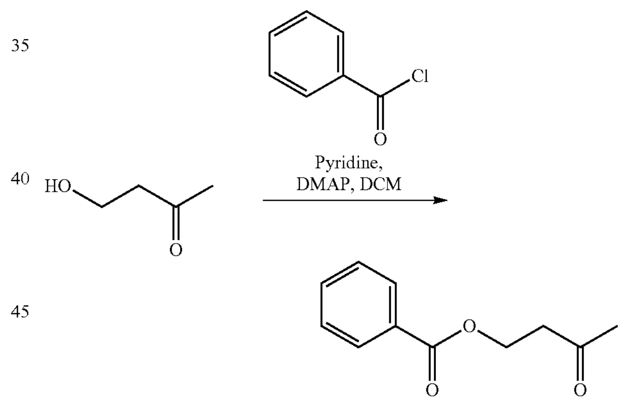

To a stirred solution of benzoyl chloride (0.396 L, 3405 mmol) in DCM (1 L) at −70° C. under nitrogen atmosphere was added pyridine (470 mL) drop-wise over a period of 1 h. After stirring for 30 min at same temperature, 4-hydroxybutan-2-one (250.0 g, 2837 mmol) in DCM (500 mL) was added dropwise over a period of 1 h. The reaction mixture was allowed to warm to 26° C. and then was stirred for 16 h. The progress of the reaction was monitored by TLC ($SiO_2$, 30% EtOAc/Pet. Rf=0.4). On completion, the reaction mixture was washed with water (2×1000 mL), 1N HCl (2×500 mL) and then saturated $NaHCO_3$ solution (2×500 mL). The organic layer was dried over $Na_2SO_4$, filtered and concentrated under reduced pressure to afford 3-oxobutyl benzoate as a pale-yellow liquid (400 g, yield=69%). $^1H$ NMR (400 MHz, CHLOROFORM-d) δ=8.05-7.94 (m, 2H), 7.60-7.51 (m, 1H), 7.47-7.36 (m, 2H), 4.65-4.54 (t, 2H), 2.97-2.84 (t, 2H), 2.28-2.13 (s, 3H). HPLC purity=94.1%.

Step 2: Preparation of 3,3-difluorobutyl benzoate

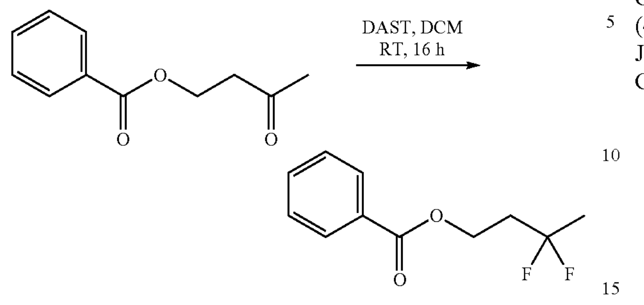

To the stirred solution of 3-oxobutyl benzoate (90 g, 427 mmol) in dichloromethane (700 mL) at 0° C. under nitrogen atmosphere was added DAST (677 mL, 5125 mmol) dropwise over a period of 1 h. The reaction mixture was warmed to 26° C. and stirred for 16 hr. The progress of reaction was monitored by TLC ($SiO_2$, 20% EtOAc/Pet. Rf=0.6). On completion, the reaction mixture was diluted with DCM (500 mL) and slowly poured into cold aq. saturated $NaHCO_3$ (1 L) solution. The organic layer was separated and washed with brine solution (400 mL), dried over anhydrous $Na_2SO_4$, filtered and concentrated under reduced pressure to afford the crude compound as a yellow liquid (95 g). This material was purified by column chromatography using silica gel (100-200 mesh), eluted with 0-5% EtOAc in pet. The fractions containing product were collected and concentrated under reduced pressure to afford 3,3-difluorobutyl benzoate as a brown liquid (60 g, yield=59%,). $^1$H NMR (400 MHz, $CDCl_3$) δ=8.06-8.01 (m, 2H), 7.60-7.54 (m, 1H), 7.48-7.40 (m, 2H), 4.54-4.48 (t, 2H), 2.43-2.29 (m, 2H), 1.77-1.64 (m, 3H). LCMS purity=89.74%; m/z=215.33.

Step 3: Preparation of 3,3-difluorobutan-1-ol

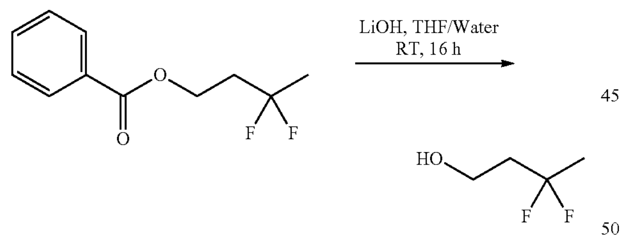

To a stirred solution of 3,3-difluorobutyl benzoate (100 g, 467 mmol) in THF (800 mL) at 0° C. under nitrogen atmosphere was added a solution of lithium hydroxide monohydrate (137 g, 3268 mmol) in water (800 mL). The reaction mixture was allowed to warm to 26° C. and then was stirred for 16 hr. The progress of the reaction was monitored by TLC ($SiO_2$, 20% EtOAc/Pet. Rf=0.6, $KMnO_4$ active). On completion, the reaction mixture was diluted with diethyl ether (400 mL). The organic layer was separated and the aqueous layer was again extracted with diethyl ether (300 mL). The combined organics were washed with brine (200 mL), dried over $Na_2SO_4$, filtered and concentrated under reduced pressure (volatile product, bath temperature=25° C.) to afford the crude compound as a black liquid. This material was diluted with diethyl ether (100 mL) and treated with charcoal. The mixture was filtered through a pad of Celite. The Celite pad was extracted with diethyl ether (200 mL). The combined filtrates were concentrated under reduced pressure (volatile product, bath temperature=25° C.) to afford 3,3-difluorobutan-1-ol as a pale-yellow liquid (40 g, yield=71%). $^1$H-NMR (400 MHz, $CDCl_3$) δ=3.87 (t, J=6.1 Hz, 2H), 2.22-2.07 (m, 2H), 1.73-1.57 (m, 3H). GCMS Purity=91.3%; m/z=110.0.

Preparation of 2-amino-6-(3,3-difluorobutoxy)nicotinic acid

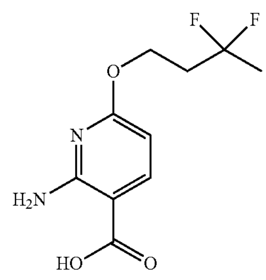 [SMILES: CC(F)(F)CCOc1ccc(C(=O)O)c(N)n1]

Synthesis Scheme:

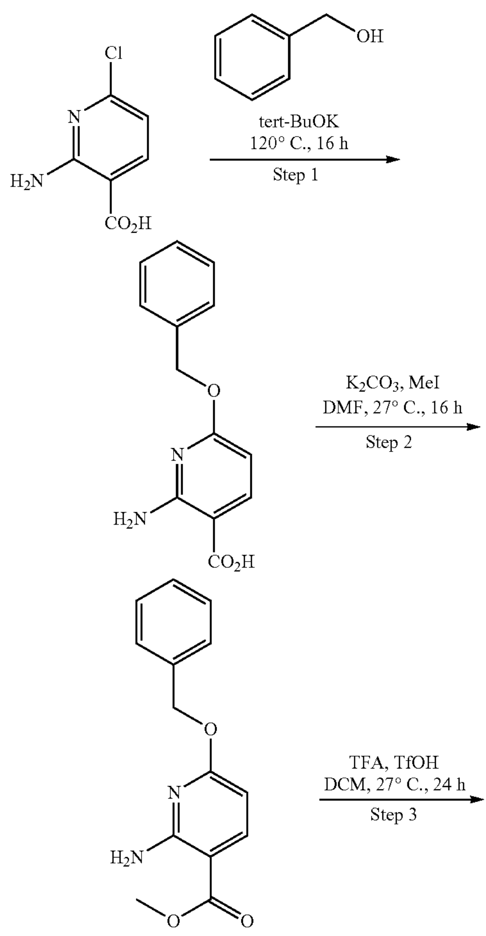

-continued

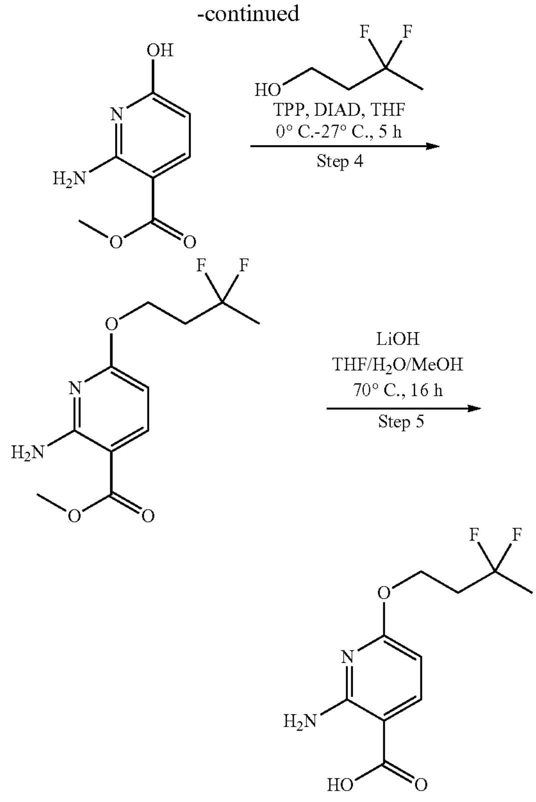

Step 1: Preparation of 2-amino-6-(benzyloxy) nicotinic acid

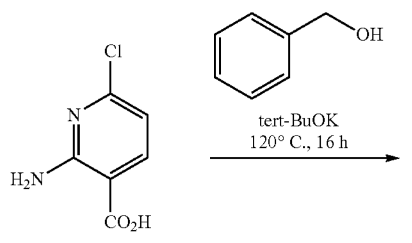

To a stirred solution of 2-amino-6-chloronicotinic acid (200 g, 1159 mmol) in benzyl alcohol (1400 mL, 13464 mmol) at 26° C. under $N_2$ atmosphere was added potassium tert-butoxide (390 g, 3477 mmol). The reaction mixture was heated to 120° C. and stirred for 16 hr at that temperature. The progress of reaction was monitored by TLC ($SiO_2$, 10% MeOH in DCM, Rf=0.5). On completion, the reaction mixture was diluted with water (3 L) and extracted with diethyl ether (2×1000 mL). The organic layer was separated and the aqueous layer was acidified to pH 4 using aq. citric acid solution (0.5 M). The precipitated solid was collected by filtration and then dried under reduced pressure to afford 2-amino-6-(benzyloxy) nicotinic acid as an off-white solid (220 g, yield=72%). $^1H$ NMR (400 MHz, DMSO-$d_6$) δ=12.56-12.32 (m, 1H), 7.97-7.91 (m, 1H), 7.52-7.41 (m, 2H), 7.38-7.11 (m, 5H), 6.03 (d, J=8.5 Hz, 1H), 5.39-5.31 (m, 2H). LCMS Purity=93%; m/z=245.29 (M+H).

Step 2: Preparation of methyl 2-amino-6-(benzyloxy)nicotinate

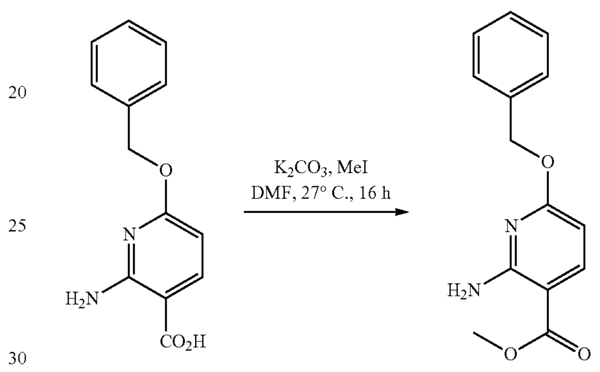

To a stirred solution of 2-amino-6-(benzyloxy)nicotinic acid (220 g, 901 mmol) in DMF (2.5 L) at 26° C. under $N_2$ atmosphere were slowly added potassium carbonate (373 g, 2702 mmol) and iodomethane (0.282 L, 4504 mmol). The reaction mixture was stirred at 27° C. for 16 hr. The progress of reaction was monitored by TLC ($SiO_2$, 40% EtOAc/Pet., Rf=0.6). On completion, the reaction mixture was diluted with water (5 L). The precipitated solid was isolated by filtration and then dried under vacuum to afford methyl 2-amino-6-(benzyloxy)nicotinate as an off-white solid (220 g, yield=92%). $^1H$ NMR (400 MHz, $CDCl_3$) δ=8.00 (d, J=8.4 Hz, 1H), 7.42-7.40 (m, 2H), 7.39-7.35 (m, 2H), 7.34-7.31 (m, 1H), 6.01 (d, J=8.4 Hz, 1H), 5.33 (s, 2H), 3.84 (s, 3H). LCMS Purity=97%, m/z=259.30 (M+H).

Step 3: Preparation of methyl 2-amino-6-hydroxynicotinate

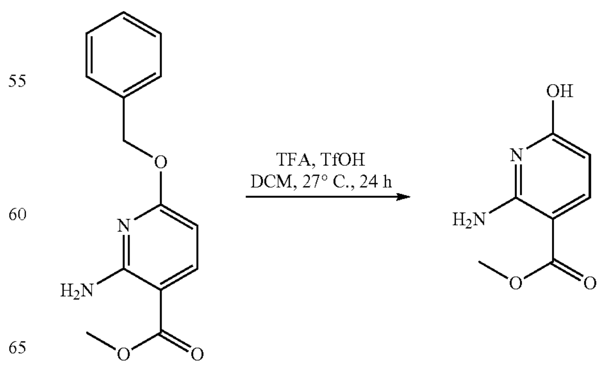

To a stirred solution of methyl 2-amino-6-(benzyloxy) nicotinate (50 g, 190 mmol) in DCM (500 mL) at 26° C. under $N_2$ atmosphere were slowly added TFA (800 mL) and triflic acid (25 mL, 282 mmol). The reaction mixture was stirred at 26° C. for 16 hr. The progress of reaction was monitored by TLC ($SiO_2$, EtOAc, Rf=0.2). On completion, the volatiles were removed under vacuum to afford the crude product. This material was triturated with diethyl ether (3×1000 mL) and the precipitated solid was then isolated by filtration. To the solid was added water (2 L) and the mixture was then 5 h. The solid was collected by filtration and was washed with water. The solid was dried under vacuum to afford methyl 2-amino hydroxynicotinate as an off-white solid (25 g, yield=78%). 1H NMR (300 MHz, DMSO-$d_6$) δ=10.92-10.76 (m, 1H), 7.65 (d, J=9.5 Hz, 1H), 7.43-6.87 (m, 2H), 5.51 (d, J=9.5 Hz, 1H), 3.69 (s, 3H). LCMS Purity=99.32%; m/z=169.32 (M+H). The absence of TFA and triflic acid in the product was confirmed by $^{19}$F-NMR. The product was used directly in the next step without additional purification.

Step 4: Preparation of methyl 2-amino-6-(3,3-difluorobutoxy)nicotinate

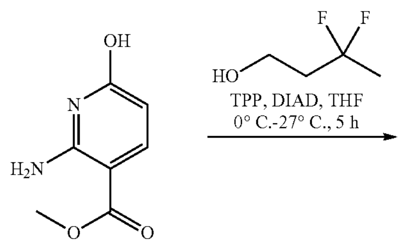

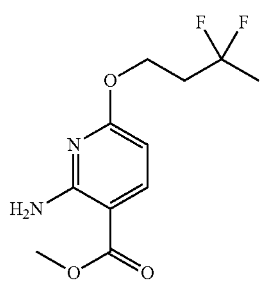

To a stirred solution of methyl 2-amino-6-hydroxynicotinate (25 g, 147 mmol) in THF (375 mL) at 0° C. under $N_2$ atmosphere were added triphenylphosphine (77 g, 294 mmol) and then drop-wise DIAD (57.2 mL, 294 mmol). The reaction mixture was stirred for 15 min at 0° C., then to the mixture was added drop-wise at 0° C. a solution of 3,3-difluorobutan-1-ol (25.3 g, 221 mmol) in THF (125 mL). The reaction mixture was allowed to 27° C. and then was stirred for 5 h. The progress of reaction was monitored by TLC ($SiO_2$, EtOAc, Rf=0.5). On completion, the reaction mixture was concentrated under reduced pressure to afford the crude product. This material was stirred in MTBE:pet. (1:1, 1 L). The mixture was filtered and the filter pad was extracted with MTBE:pet. (1:1, 4×200 mL). The combined filtrate was concentrated under reduced pressure to afford a pale-yellow gummy solid. This material was purified by column chromatography using silica gel (100-200 mesh), eluted with 10-20% EtOAc in pet. The fractions containing product were collected and concentrated under reduced pressure to afford methyl 2-amino-6-(3,3-difluorobutoxy) nicotinate as a pale-yellow liquid (20 g, yield=48%). $^1$H NMR (400 MHz, $CDCl_3$) δ=8.05-7.95 (m, 1H), 6.02 (d, J=8.8 Hz, 1H), 4.45 (t, J=6.8 Hz, 2H), 3.80 (s, 3H), 2.40-2.22 (m, 2H), 1.68 (t, J=18.6 Hz, 3H). LCMS purity=91.1%, m/z=261.25 (M+H).

Step 5: Preparation of 2-amino-6-(3,3-difluorobutoxy)nicotinic acid

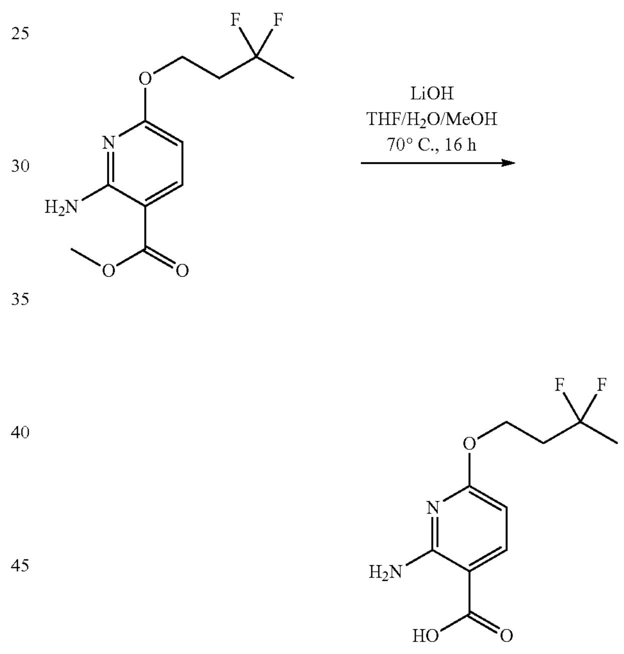

To a stirred solution of methyl 2-amino-6-(3,3-difluorobutoxy)nicotinate (5.7 g, 20.81 mmol) in THF (120 mL) and Methanol (30 mL) at 26° C. was added a solution of LiOH (2.491 g, 104 mmol) in water (30 mL). The reaction mixture was heated to 70° C. and stirred at that temperature for 16 h. The progress of reaction was monitored by TLC ($SiO_2$, 50% EtOAc/Pet Rf=0.2). On completion, the reaction mixture was concentrated under reduced pressure. The resulting residue was dissolved in water (60 mL) and acidified to pH 4 using 1N HCl. The mixture was extracted with ethyl acetate (3×100 mL). The combined organics were washed with brine (100 mL), dried over anhydrous $Na_2SO_4$, and concentrated under reduced pressure to afford 2-amino-6-(3,3-difluorobutoxy)nicotinic acid as a brown solid (4.6 g, yield=87%). $^1$H NMR (400 MHz, $CDCl_3$) δ=11.66-10.84 (m, 1H), 8.12-7.97 (m, 1H), 6.07 (d, J=8.3 Hz, 1H), 4.52-4.36 (m, 2H), 2.41-2.28 (m, 2H), 1.68 (t, J=18.6 Hz, 3H). LCMS Purity=97.68%, m/z=247.24 (M+H).

Preparation of tert-Butyl (S)-(1-(3-(4-chloro-3-(N-(4-methoxybenzyl)methylsulfonamido)-1-methyl-1H-indazol-7-yl)-7-(3,3-difluorobutoxy)-4-oxo-3,4-dihydropyrido[2,3-d]pyrimidin-2-yl)-2-(3,5-difluorophenyl)ethyl)carbamate

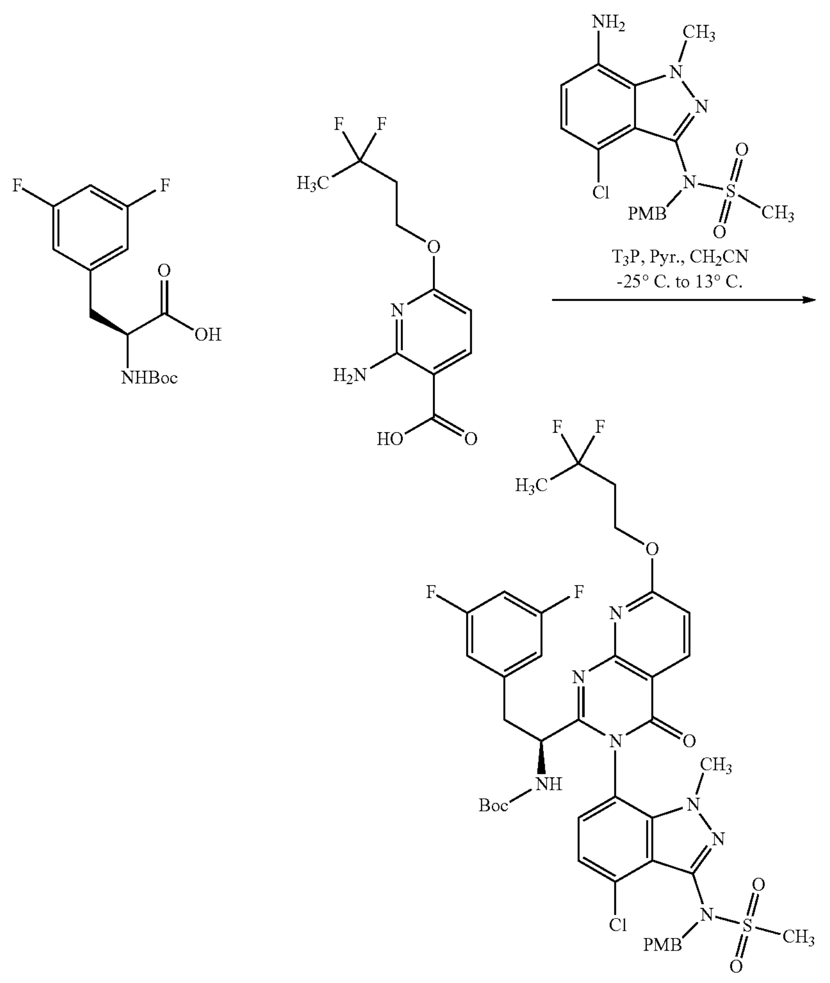

To a stirred solution of (S)-2-((tert-butoxycarbonyl)amino)-3-(3,5-difluorophenyl)propanoic acid (50 g, 166 mmol) and 2-amino-6-(3,3-difluorobutoxy)nicotinic acid (41.3 g, 166 mmol) in acetonitrile (1000 mL) under nitrogen atmosphere at −25° C. was added pyridine (47.0 mL, 581 mmol). To the resulting mixture was added 2,4,6-tripropyl-1,3,5,2,4,6-trioxatriphosphinane 2,4,6-trioxide ("T3P", 50% wt in EtOAc, 494 mL, 830 mmol) drop-wise over 15 min. The solution was allowed to warm to 13° C. and was then stirred for 5 hrs. To the solution at 13° C. was added N-(7-amino-4-chloro-1-methyl-1H-indazol-3-yl)-N-(4-methoxybenzyl)methanesulfonamide (62.3 g, 158 mmol). The reaction mass was then allowed to slowly warm to 27° C. and then was stirred at that temperature for 48 hrs. The progress of the reaction was monitored by TLC ($SiO_2$, 50% EtOAc/Pet., Rf=0.4). On completion, the reaction mixture was concentrated under reduced pressure and the residue was added drop-wise into saturated aqueous $NaHCO_3$ solution (1000 mL) at 0° C. A white precipitate was formed which was collected by vacuum filtration. The isolated solids were washed with water (2 L). Vacuum filtration was maintained until most residual water had been removed from the solids. The solids were then dissolved in DCM (2 L). The solution was dried over $Na_2SO_4$, filtered and then concentrated under reduced pressure to afford the crude product. This material was purified by silica gel chromatography eluting with 50-65% EtOAc in Pet. The fractions containing the desired product were pooled and concentrated under reduced pressure to afford tert-butyl (S)-(1-(3-(4-chloro-3-(N-(4-methoxybenzyl)methylsulfonamido)-1-methyl-1H-indazol-7-yl)-7-(3,3-difluorobutoxy)-4-oxo-3,4-dihydropyrido[2,3-d]pyrimidin-2-yl)-2-(3,5-difluorophenyl)ethyl) carbamate as a yellow foamy solid (50 g, Yield=31%). The above procedure was repeated seven more times on the same scale to produce in total 592 g of the product. The combined product (592 g) was dissolved in MeOH (1 L). The solution was diluted with n-hexane (6 L). An off-white solid precipitated and then suspension was stirred for 20 min. The solid was collected by vacuum filtration while the filtrate was reserved. The solid was dried under vacuum to afford tert-butyl (S)-(1-(3-(4-chloro-3-(N-(4-methoxybenzyl)methylsulfonamido)-1-methyl-1H-indazol-7-yl)-7-(3,3-difluorobutoxy)-4-oxo-3,4-dihydropyrido[2,3-d]pyrimidin-2-yl)-2-(3,5-difluorophenyl)ethyl)carbamate as an off-white solid (300 g, Yield=48%) as an off-white solid. The product is a mixture of homochiral atropisomers (diastereomers). LCMS analysis method: Column=X Bridge BEH C18 (50 mm×4.6 mm, 2.5 μm particles); Mobile Phase A=5 mM Ammonium Bicarbonate; Mobile Phase B=acetonitrile; Gradient profile (time (min)/% B)=0/5, 0.5/5, 1.5/15, 7/98, 9/98, 9.5/5, 10/5; Column Temp=35° C.; Flow rate=1.3 mL/min. LCMS result: retention time=6.20 mins.; observed ion=888.09 (M+H); LCMS Purity=95%. Note: The reserved filtrate was concentrated and dried under vacuum to afford the product (120 g, a pale yellow solid) which was also used in downstream chemistry separately from the product described above.

Preparation of (S)—N-((6P)-7-(2-(1-amino-2-(3,5-difluorophenyl)ethyl)-7-(3,3-difluorobutoxy)-4-oxopyrido[2,3-d]pyrimidin-3(4H)-yl)-4-chloro-1-methyl-1H-indazol-3-yl)methanesulfonamide

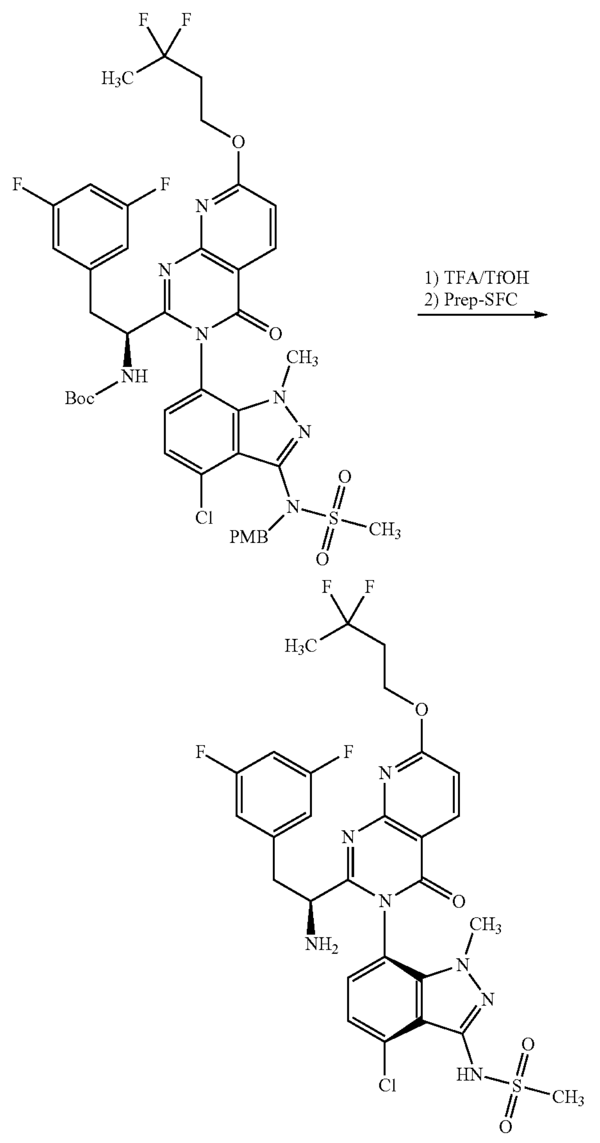

To a stirred solution of tert-butyl (S)-(1-(3-(4-chloro-3-(N-(4-methoxybenzyl)methylsulfonamido)-1-methyl-1H-indazol-7-yl)-7-(3,3-difluorobutoxy)-4-oxo-3,4-dihydropyrido[2,3-d]pyrimidin-2-yl)-2-(3,5-difluorophenyl)ethyl) carbamate (95% purity, 300 g, 321 mmol) in DCM (3000 mL) were added at 0° C. trifluoroacetic acid (TFA) (900 mL) followed by triflic acid (158 mL, 1782 mmol). The solution was allowed to warm to 27° C. and was then stirred for 2 hrs under nitrogen atmosphere. The progress of the reaction was monitored by TLC ($SiO_2$, 80% EtOAc/Pet. Rf=0.3). On completion, the volatiles were removed under a gentle stream of nitrogen gas. The residue was added into saturated $NaHCO_3$ solution (1000 mL) at 0° C. The was adjusted to solution pH ~8 by addition of solid $NaHCO_3$. The mixture was extracted with EtOAc (5×1000 mL). The combined organic layers were dried over $Na_2SO_4$, filtered, and then concentrated under reduced pressure to afford the crude product. This material was purified by silica gel chromatography eluting with 5-10% MeOH in DCM. The fractions containing the desired product were pooled and concentrated under reduced pressure to afford (S)—N-(7-(2-(1-amino-2-(3,5-difluorophenyl)ethyl)-7-(3,3-difluorobutoxy)-4-oxopyrido[2,3-d]pyrimidin-3(4H)-yl)-4-chloro-1-methyl-1H-indazol-3-yl)methanesulfonamide (211 g, brown foamy solid) as a mixture of homochiral atropisomers (diastereomers, Major: 79% and Minor: 10% by LCMS). The material was dissolved in methanol:acetonitrile (80:20, 1800 mL) and was then purified by prep-SFC using the following method: Column=(R,R) WHELK-01 (30×250 mm, 5 μm particles); eluent=$CO_2$:MeOH (60:40); Flow-rate=90 g/min; Back-pressure=100 bar; Detection=214 nm (UV); Stack time=15.5 min; Load per injection=1.125 gram. The pure major peak was collected and concentrated under reduced pressure to afford (S)—N-((6P)-7-(2-(1-amino-2-(3,5-difluorophenyl)ethyl)-7-(3,3-difluorobutoxy)-4-oxopyrido[2,3-d]pyrimidin-3(4H)-yl)-4-chloro-1-methyl-1H-indazol-3-yl)methanesulfonamide (151 g, Yield=69%) as a brown solid. The product is a single stereoisomer. 1H-NMR (400 MHz, DMSO-$d_6$) δ: 8.41 (d, J=8.8 Hz, 1H), 7.39 (dd, J=22.4, 7.9 Hz, 2H), 7.05 (d, J=8.3 Hz, 1H), 7.03-6.98 (m, 1H), 6.72 (d, J=8.8 Hz, 2H), 4.66-4.63 (m, 2H), 3.67 (s, 3H), 3.54-3.50 (m, 1H), 3.28-3.23 (m, 1H), 3.21 (s, 3H), 2.88-2.82 (m, 1H), 2.56-2.52 (m, 1H), 2.47-2.44 (m, 1H), 1.73 (t, J=19.0 Hz, 3H); LCMS method: Column=Acquity BEH C18 (50 mm×2.1 mm, 1.7 μm particles); Mobile Phase A=0.1% Formic Acid in water; Mobile Phase B=0.1% Formic Acid in MeCN; Gradient profile (time (min)/% B): 0/3, 0.4/3, 3.2/98, 3.8/98, 4.2/3, 4.5/3; Column Temp=35° C.; Flow rate: 0.6 mL/min. LCMS result: retention time=1.93 mins.; observed ion=668.05 (M+H); HPLC Purity=98%; Chiral HPLC Purity=96.9%.

Preparation of (S)—N-((6P)-7-(2-(1-amino-2-(3,5-difluorophenyl)ethyl)-4-oxo-7-(3,3,3-trifluoro-propoxy)pyrido[2,3-d]pyrimidin-3(4H)-yl)-4-chloro-1-methyl-1H-indazol yl)methanesulfonamide

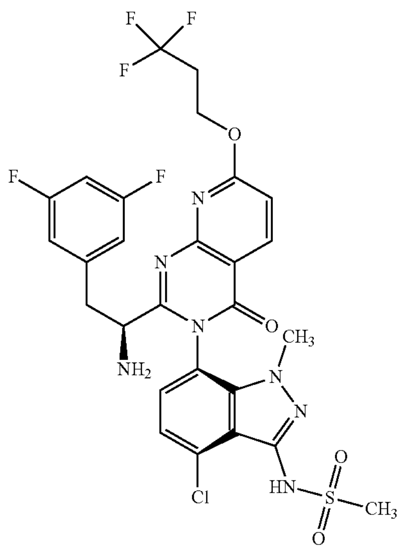

The title compound was prepared following the synthesis pathway and procedures used to prepare (S)—N-((6P)-7-(2-(1-amino-2-(3,5-difluorophenyl)ethyl)-7-(3,3-difluorobutoxy)-4-oxopyrido[2,3-d]pyrimidin-3(4H)-yl)-4-chloro-1-methyl-1H-indazol-3-yl)methanesulfonamide substituting 2-amino-6-(3,3,3-trifluoropropoxy)nicotinic acid for 2-amino-6-(3,3-difluorobutoxy)nicotinic acid; 2-amino-6-(3,3,3-trifluoropropoxy)nicotinic acid was prepared according to the synthesis pathway and procedures used to prepare 2-amino-6-(3,3-difluorobutoxy)nicotinic acid substituting 3,3,3-trifluoropropan-1-ol for 3,3-difluorobutan-1-ol.

HPLC Purification:

HPLC purification was performed using one of the conditions indicated below, optionally followed by a second HPLC purification using a different condition indicated below. Based on analytical HPLC data obtained on the crude reaction mixture, the purification condition was optimized for each target compound by modifying the initial Solvent A:Solvent B ratio, the gradient time, the final Solvent A:Solvent B ratio, and the hold time at the final Solvent A:Solvent B concentration.

HPLC Condition A: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Wavelength=215 and 254 nm. ESI+ Range: 150 to 1500 Dalton.

HPLC Condition B: Column: Sunfire prep C18 OBD, 30×100 mm, 5 μm particles; Solvent A: water:MeCN 95:5 w/0.1% TFA, Solvent B: MeCN:water 95:5 w/0.1% TFA. Flow Rate=42 mL/min. Wavelength=220 and 254 nm.

HPLC Condition C: Column: Waters Xterra C18, 19×100 mm, 10 μm particles; Solvent A=0.1% $NH_4OH$ in 100% Water. Solvent B=Acetonitrile. Flow Rate=40 mL/min. Wavelength=215 and 254 nm. ESI+ Range: 150 to 1500 Dalton.

General LMCS Analysis Methods:

LCMS Method A:

Column: Acquity CSH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm. ESI+ Range: 150 to 1500 Dalton. System: Agilent 1290 Infinity II Preparation of Example 1: N—((S)-1-((3P)-3-(4-chloro-1-methyl-3-(methylsulfonamido)-1H-indazol-7-yl)-7-(3,3-difluorobutoxy)-4-oxo-3,4-dihydro-pyrido[2,3-d]pyrimidin-2-yl)-2-(3,5-difluorophenyl)ethyl)-2-((3bS,4aR)-3-cyclopropyl-5,5-difluoro-3b,4,4a,5-tetrahydro-1H-cyclopropa[3,4]cyclopenta[1,2-c]pyrazol-1-yl)acetamide

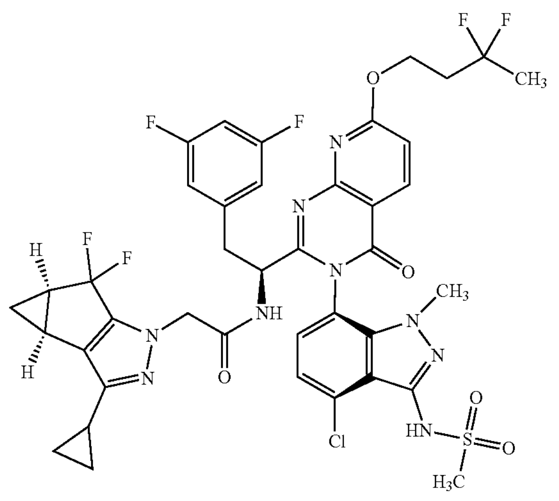

To a mixture of (S)—N-((6P)-7-(2-(1-amino-2-(3,5-difluorophenyl)ethyl)-7-(3,3-difluorobutoxy)-4-oxopyrido[2,3-d]pyrimidin-3(4H)-yl)-4-chloro-1-methyl-1H-indazol-3-yl)methanesulfonamide (0.03 g, 0.045 mmol), 2-(3H-[1,2,3]triazolo[4,5-b]pyridin-3-yl)-1,1,3,3-tetramethylisouronium hexafluorophosphate(V) ("HATU", 0.018 g, 0.046 mmol) and 2-((3bS,4aR)-3-cyclopropyl-5,5-difluoro-3b,4,4a,5-tetrahydro-1H-cyclopropa[3,4]cyclopenta[1,2-c]pyrazol-1-yl)acetic acid (10.3 mg, 0.045 mmol) in tetrahydrofuran (THF) was added N-ethyl-N-isopropylpropan-2-amine (0.024 ml, 0.135 mmol). The mixture was stirred at room temperature for 18 hr. The reaction mixture was concentrated under reduced pressure. The resulting residue was dissolved in DMF and then filtered. The filtrate was subjected to HPLC purification to afford N—((S)-1-((3P)-3-(4-chloro-1-methyl-3-(methylsulfonamido)-1H-indazol-7-yl)-7-(3,3-difluorobutoxy)-4-oxo-3,4-dihydropyrido[2,3-d]pyrimidin-2-yl)-2-(3,5-difluorophenyl)ethyl)-2-((3bS,4aR)-3-cyclopropyl-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=1.5 min.; observed ion=904.4 (M+H). 1H NMR (500 MHz, METHANOL-d4) δ ppm 8.34-8.40 (m, 1H) 7.17-7.24 (m, 1H) 7.06-7.13 (m, 1H) 6.92-7.01 (m, 1H) 6.62-6.73 (m, 1H) 6.43-6.52 (m, 2H) 4.61-4.76 (m, 3H) 4.26-4.40 (m, 2H) 3.48-3.53 (m, 3H) 3.29-3.37 (m, 1H) 3.15-3.16 (m, 3H) 2.96-3.01 (m, 1H)

2.37-2.47 (m, 2H) 2.10-2.23 (m, 2H) 1.68-1.75 (m, 1H) 1.59-1.68 (m, 3H) 1.16-1.20 (m, 1H) 0.75-0.82 (m, 4H) 0.64-0.68 (m, 2H).

Preparation of Example 2: N—((S)-1-((3P)-3-(4-chloro-1-methyl-3-(methylsulfonamido)-1H-indazol-7-yl)-7-(3,3-difluorobutoxy)-4-oxo-3,4-dihydro-pyrido[2,3-d]pyrimidin-2-yl)-2-(3,5-difluorophenyl) ethyl)-2-((3bR,4aS)-3-cyclopropyl-5,5-difluoro-3b,4,4a,5-tetrahydro-1H-cyclopropa[3,4]cyclopenta[1,2-c]pyrazol-1-yl)acetamide

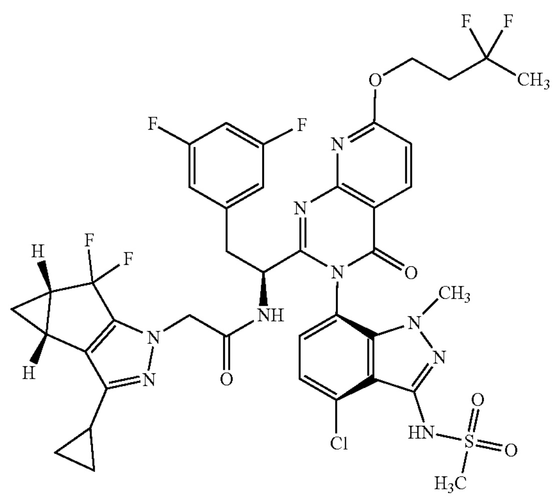

To a mixture of (S)—N-((6P)-7-(2-(1-amino-2-(3,5-difluorophenyl)ethyl)-7-(3,3-difluorobutoxy)-4-oxopyrido[2,3-d]pyrimidin-3(4H)-yl)-4-chloro-1-methyl-1H-indazol-3-yl)methanesulfonamide (0.03 g, 0.045 mmol), 2-(3H-[1,2,3]triazolo[4,5-b]pyridin-3-yl)-1,1,3,3-tetramethylisouronium hexafluorophosphate(V) ("HATU", 0.018 g, 0.046 mmol) and 2-((3bR,4aS)-3-cyclopropyl-5,5-difluoro-3b,4,4a,5-tetrahydro-1H-cyclopropa[3,4]cyclopenta[1,2-c]pyrazol-1-yl)acetic acid (10.3 mg, 0.045 mmol) in tetrahydrofuran (THF) was added N-ethyl-N-isopropylpropan-2-amine (0.024 ml, 0.135 mmol). The mixture was stirred at room temperature for 18 hr. The reaction mixture was concentrated under reduced pressure. The resulting residue was dissolved in DMF and then filtered. The filtrate was subjected to HPLC purification to afford N—((S)-1-((3P)-3-(4-chloro-1-methyl-3-(methylsulfonamido)-1H-indazol-7-yl)-7-(3,3-difluorobutoxy)-4-oxo-3,4-dihydro-pyrido[2,3-d]pyrimidin-2-yl)-2-(3,5-difluorophenyl)ethyl)-2-((3bR,4aS)-3-cyclopropyl-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=1.51 min.; observed ion=904.4 (M+H). 1H NMR (500 MHz, METHANOL-d4) δ ppm 8.34-8.42 (m, 1H) 7.19-7.26 (m, 1H) 7.11-7.18 (m, 1H) 6.92-6.99 (m, 1H) 6.62-6.72 (m, 1H) 6.40-6.49 (m, 2H) 4.70-4.74 (m, 1H) 4.62-4.68 (m, 2H) 4.29-4.38 (m, 2H) 3.50-3.53 (m, 3H) 3.29-3.34 (m, 1H) 3.15-3.17 (m, 3H) 2.94-3.00 (m, 1H) 2.36-2.48 (m, 2H) 2.10-2.22 (m, 2H) 1.70-1.78 (m, 1H) 1.58-1.68 (m, 3H) 1.13-1.17 (m, 1H) 0.76-0.86 (m, 4H) 0.64-0.73 (m, 2H).

Preparation of Example 3: N—((S)-1-((3P)-3-(4-chloro-1-methyl-3-(methylsulfonamido)-1H-indazol-7-yl)-4-oxo-7-(3,3,3-trifluoropropoxy)-3,4-dihydro-pyrido[2,3-d]pyrimidin-2-yl)-2-(3,5-difluorophenyl) ethyl)-2-((3bS,4aR)-3-cyclopropyl-5,5-difluoro-3b,4,4a,5-tetrahydro-1H-cyclopropa[3,4]cyclopenta[1,2-c]pyrazol-1-yl)acetamide

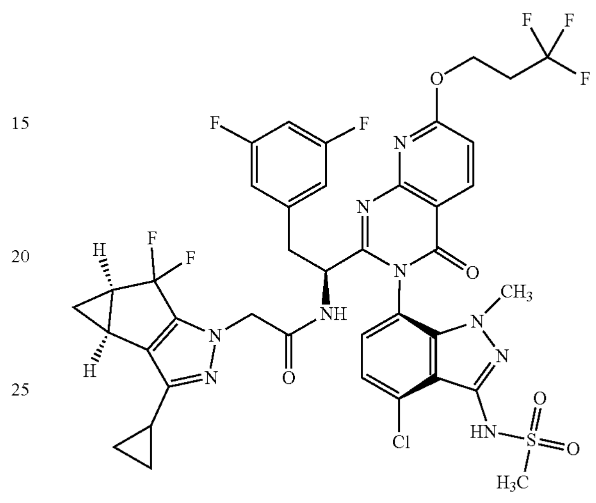

To a stirred solution of (S)—N-((6P)-7-(2-(1-amino-2-(3,5-difluorophenyl)ethyl)-4-oxo-7-(3,3,3-trifluoropropoxy) pyrido[2,3-d]pyrimidin-3(4H)-yl)-4-chloro-1-methyl-1H-indazol-3-yl)methanesulfonamide (0.05 g, 0.074 mmol) in tetrahydrofuran (THF) (1 mL)/N,N-dimethylformamide (DMF) (0.2 mL) were added 2-((3bS,4aR)-3-cyclopropyl-5,5-difluoro-3b,4,4a,5-tetrahydro-1H-cyclopropa[3,4]cyclopenta[1,2-c]pyrazol-1-yl)acetic acid (0.020 g, 0.078 mmol), 2-(3H-[1,2,3]triazolo[4,5-b]pyridin-3-yl)-1,1,3,3-tetramethylisouronium hexafluorophosphate(V) ("HATU", 0.034 g, 0.089 mmol) and DIPEA (0.019 mL, 0.112 mmol). The reaction mixture was stirred at rt for 3 h. To the reaction was added ammonia in methanol (2 M, 1 mL). The mixture was stirred for 2 h, then was concentrated under reduced pressure. The resulting residue was dissolved in DMF (2 mL) and filtered. The filtrate was subjected to HPLC purification to afford N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-cyclopropyl-5,5-difluoro-3b,4,4a,5-tetrahydro-1H-cyclopropa[3,4] cyclopenta[1,2-c]pyrazol-1-yl)acetamide. The sample was analyzed using LCMS Method A: retention time=1.48 min.; observed ion=908.4 (M+H). 1H NMR (500 MHz, METHANOL-d4) δ ppm 8.50 (d, J=8.64 Hz, 1H) 7.31 (d, J=8.05 Hz, 1H) 7.21 (d, J=8.05 Hz, 1H) 7.07 (d, J=8.94 Hz, 1H) 6.75-6.81 (m, 1H) 6.58 (dd, 3=8.20, 2.24 Hz, 2H) 4.77-4.83 (m, 3H) 4.38-4.48 (m, 2H) 3.60 (s, 3H) 3.43 (dd, J=14.16, 4.32 Hz, 1H) 3.25 (s, 3H) 3.08 (dd, J=14.01, 9.54 Hz, 1H) 2.79-2.91 (m, 2H) 2.19-2.33 (m, 2H) 1.77-1.85 (m, 1H) 1.22-1.30 (m, 1H) 0.86-0.93 (m, 3H) 0.76 (dt, J=5.22, 2.01 Hz, 2H).

Preparation of Example 4: N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bR,4aS)-3-cyclopropyl-5,5-difluoro-3b,4,4a,5-tetrahydro-1H-cyclopropa[3,4]cyclopenta[1,2-c]pyrazol-1-yl)acetamide

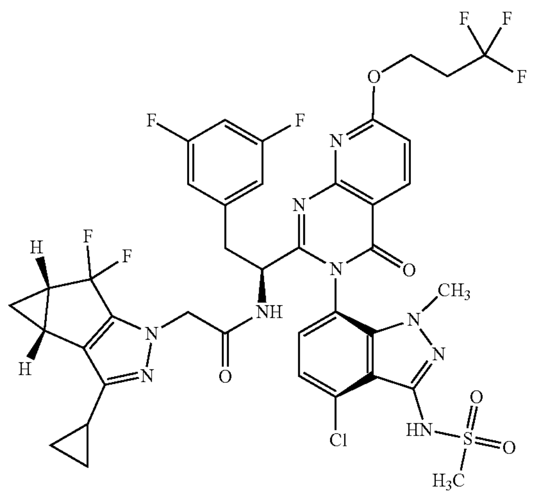

To a solution of (S)—N-((6P)-7-(2-(1-amino-2-(3,5-difluorophenyl)ethyl)-4-oxo-7-(3,3,3-trifluoropropoxy)pyrido[2,3-d]pyrimidin-3(4H)-yl)-4-chloro-1-methyl-1H-indazol-3-yl)methanesulfonamide (0.025 g, 0.037 mmol) in tetrahydrofuran (THF)) were added 2-((3bR,4aS)-3-cyclopropyl-5,5-difluoro-3b,4,4a,5-tetrahydro-1H-cyclopropa[3,4]cyclopenta[1,2-c]pyrazol-1-yl)acetic acid (9.46 mg, 0.037 mmol), DIPEA (0.019 ml, 0.112 mmol) and 2,4,6-tripropyl-1,3,5,2,4,6-trioxatriphosphinane 2,4,6-trioxide ("T3P", 50% wt. in EtOAc, 0.044 ml, 0.074 mmol). The reaction mixture was stirred for 18 h at RT. The mixture was concentrated under reduced pressure. The resulting residue was dissolved in DMF (2 mL) and filtered. The filtrate was subjected to HPLC purification to afford N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bR,4aS)-3-cyclopropyl-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=1.49 min.; observed ion=908.4 (M+H). 1H NMR (500 MHz, METHANOL-d4) δ ppm 8.50 (d, J=8.64 Hz, 1H) 7.32 (d, J=7.75 Hz, 1H) 7.23-7.27 (m, 1H) 7.07 (d, 3=8.64 Hz, 1H) 6.74-6.81 (m, 1H) 6.52-6.59 (m, 2H) 4.80 (br dd, 3=6.26, 2.09 Hz, 4H) 4.39-4.47 (m, 2H) 3.61 (s, 3H) 3.40-3.44 (m, 1H) 3.26 (s, 3H) 3.07 (dd, 3=14.31, 9.54 Hz, 1H) 2.80-2.90 (m, 2H) 2.19-2.31 (m, 2H) 1.83 (tt, 3=8.49, 5.07 Hz, 1H) 1.21-1.28 (m, 1H) 0.88-0.94 (m, 3H) 0.74-0.84 (m, 2H).

Biological Methods:

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 mg/ml penicillin G and up to 100 units/mL streptomycin. The 293T cells were propagated in DMEM media supplemented with 10% heat inactivated FBS, 100 mg/mL penicillin G and 100 mg/mL streptomycin. A recombinant $NL_{4-3}$ proviral clone, in which a section of the nef gene was replaced with the *Renilla* luciferase gene, was used to make the reference virus used in these studies. The recombinant virus was prepared through transfection of the recombinant $NL_{4-3}$ proviral clone into 293T cells using Transit-293 Transfection Reagent from Mirus Bio LLC (Madison, WI). Supernatent was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, WI). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where (Fa)=1/[1+($ED_{50}$/drug conc.)m] (Johnson V A, Byington R T. Infectivity Assay. In Techniques in HIV Research. ed. Aldovini A, Walker B D. 71-76. New York: Stockton Press. 1990). The 50% inhibitory concentration ($EC_{50}$) was calculated by using the exponential form of the median effect equation where percent inhibition=1/[1+($EC_{50}$/drug concentration)m], where m is a parameter that reflects the slope of the concentration-response curve.

Compound cytotoxicity and the corresponding $CC_{50}$ values were determined using the same protocol as described in the antiviral assay except that uninfected cells were used. Cytotoxicity was assessed on day 4 in uninfected MT2 cells by using an XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.).

| Example | $EC_{50}$ nM | $CC_{50}$ μM |
|---|---|---|
| Example 1 | 0.027 | >0.1 |
| Example 2 | 0.050 | >0.1 |
| Example 3 | 0.014 | >0.1 |
| Example 4 | 0.079 | >0.1 |

What is claimed is:

1. A compound or salt selected from the group consisting of:

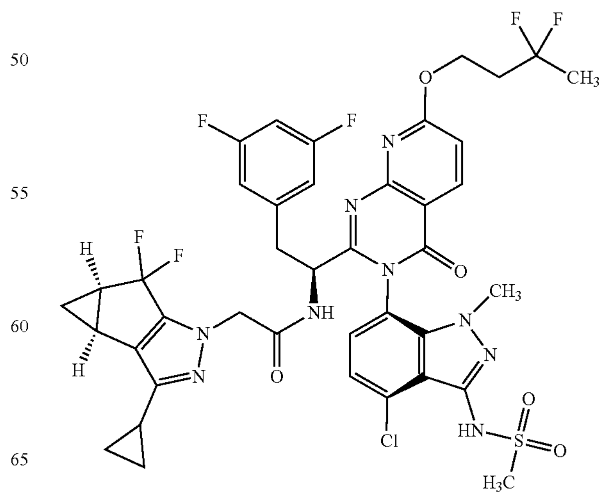

-continued

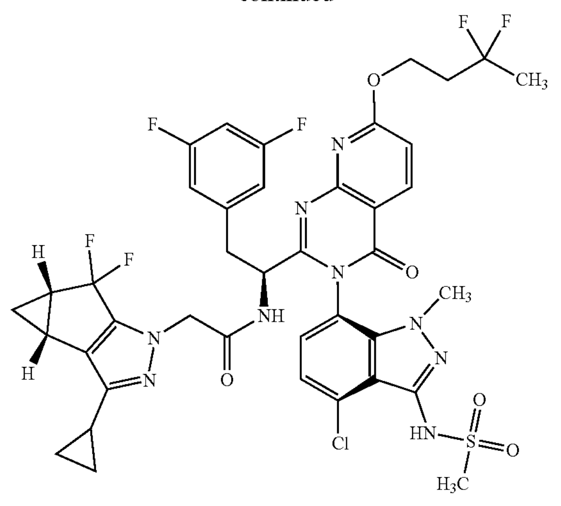

-continued

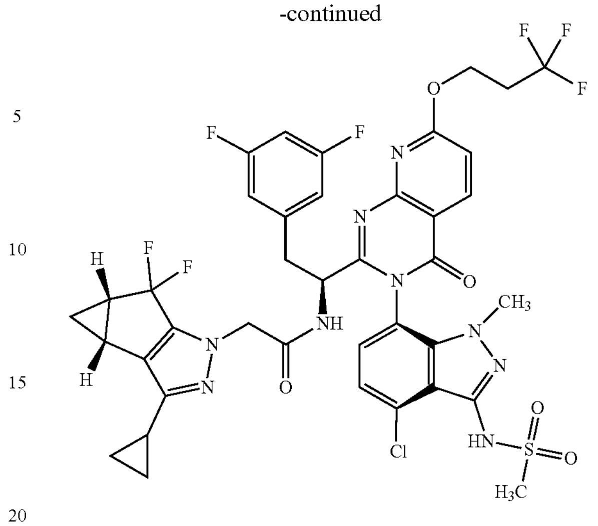

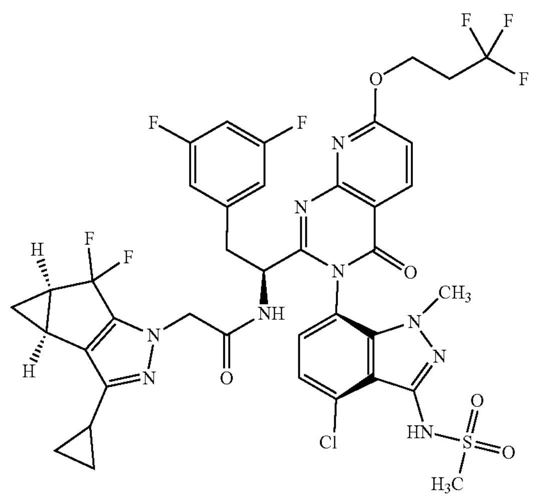

and pharmaceutically acceptable salts thereof.

2. A pharmaceutical composition comprising a compound or salt according to claim 1.

3. A composition according to claim 2 further comprising a pharmaceutically acceptable excipient.

4. A composition according to claim 2 or claim 3 suitable for oral administration, for intramuscular injection, or for subcutaneous injection.

5. A method of treating HIV infection in a human comprising administration of a compound or salt according to claim 1.

6. The method of claim 5 wherein said administration is oral.

7. The method of claim 5 wherein said administration is intramuscular injection or subcutaneous injection.

8. The method of claim 5 wherein said method further comprises administration of at least one other agent used for treatment of AIDS or HIV infection in a human.

9. The method of claim 8 wherein said at least one other agent is selected from the group consisting of dolutegravir, bictegravir, lamivudine, fostemsavir, and cabotegravir.

* * * * *